United States Patent
Pace et al.

(10) Patent No.: US 6,696,084 B2
(45) Date of Patent: Feb. 24, 2004

(54) SPRAY DRYING PROCESS AND COMPOSITIONS OF FENOFIBRATE

(75) Inventors: Gary W. Pace, Winchester, MA (US); Awadesh K. Mishra, Quebec (CA); Robert A. Snow, West Chester, PA (US); Indu Parikh, Durham, NC (US); Pol-Henri W. Guivarc'h, Quebec (CA)

(73) Assignee: RTP Pharma Inc., Durham, NC (US)

( * ) Notice: Subject to any disclaimer, the term of this patent is extended or adjusted under 35 U.S.C. 154(b) by 144 days.

(21) Appl. No.: 09/838,593

(22) Filed: Apr. 20, 2001

(65) Prior Publication Data

US 2002/0056206 A1 May 16, 2002

Related U.S. Application Data

(60) Provisional application No. 60/270,157, filed on Feb. 22, 2001, provisional application No. 60/241,761, filed on Oct. 20, 2000, and provisional application No. 60/234,186, filed on Sep. 20, 2000.

(51) Int. Cl.⁷ .............. A61K 9/14; A61K 9/20; A61K 9/48
(52) U.S. Cl. ........ 424/451; 424/458; 424/464; 424/469; 424/470; 424/489; 424/490; 252/363.5
(58) Field of Search .................. 424/489, 490, 424/493–498, 451, 458, 464, 469, 470; 252/303, 314, 363.5; 514/78

(56) References Cited

U.S. PATENT DOCUMENTS

| 5,700,471 A | 12/1997 | End et al. |
| 5,827,536 A | * 10/1998 | Laruelle |
| 5,922,355 A | * 7/1999 | Parikh |

FOREIGN PATENT DOCUMENTS

| EP | 0 807 431 A2 | 11/1997 |
| WO | WO 00/30616 | 6/2000 |
| WO | WO 00/37078 | 6/2000 |

* cited by examiner

*Primary Examiner*—Gollamudi S. Kishore
(74) *Attorney, Agent, or Firm*—Edwards & Angell, LLP

(57) ABSTRACT

The present invention relates to a novel spray drying process for the preparation of pharmaceutical compositions containing small particles of phospholipid-stabilized fenofibrate. This invention also relates to spray dried powdered compositions prepared according to this process, and to dosage forms of fenofibrate (capsules, tablets, powders, granules, and dispersions) prepared from these powdered compositions. The powdered compositions and dosage forms are useful in the treatment of dyslipidemia and dyslipoproteinemia and have the advantage that they provide reduced in vivo variability in the bioavailability of fenofibrate active species among fed and fasted patients when administered orally.

60 Claims, No Drawings

SPRAY DRYING PROCESS AND COMPOSITIONS OF FENOFIBRATE

This application claims benefit of 60/234,186, filed Sep. 20, 2000; 60/241,761 filed Oct. 20, 2000 and 60/270,157 filed Feb. 22, 2001.

BACKGROUND OF THE INVENTION

The present invention relates to a novel spray drying process for the preparation of pharmaceutical compositions containing small particles of phospholipid-stabilized fenofibrate. This invention also relates to spray dried powdered compositions prepared according to this process, and to dosage forms of fenofibrate (capsules, tablets, powders, granules, and dispersions) prepared from these powdered compositions. The powdered compositions and dosage forms are useful in the treatment of dislipidemia and dislipoproteinemia and have the advantage that they provide reduced in vivo variability in the bioavailability of fenofibrate active species among fed and fasted patients when administered orally.

In a preferred aspect, the present invention relates to a process for the preparation of an orally administered pharmaceutical composition containing microparticles of solid fenofibrate comprising the formation of a homogenized molten microdroplet aqueous suspension of fenofibrate in the presence of and stabilized by a phospholipid surface active substance and then spray drying the molten microdroplets in the presence of a bulking agent to produce solid microparticles in dried bulking agent as a powder. The powder can be further processed into an orally administerable dosage form such as a capsule, tablet, powder, or granule which provides a therapeutically effective amount of fenofibrate active species to a fasted human patient in need of treatment by fenofibrate that is greater than 80% of the quantity of fenofibrate active species provided by the same amount to the same patient when the patient is fed at least 1000 calories 50% of which are from fat.

The present invention also relates to a method of treatment of dislipidemia and dislipoproteinemia in a mammal which comprises administering to the mammal a therapeutically effective oral dosage form comprising microparticles of a solid poorly water soluble fibrate that are stabilized by a phospholipid surface active substance and prepared according to the process of this invention, wherein the dosage form provides into the blood of the mammal in a fasted state a therapeutically effective amount of the fibrate active species that is at least 90% of the AUC amount of the fibrate active species provided by the dosage form into the blood of the patient in a fed state.

The present invention also relates to novel pharmaceutical compositions containing small particles of phospholipid-stabilized fenofibrate prepared according to the process of this invention that provide reduced in vivo variability in the bioavailability of the fenofibrate active species among fed and fasted patients when administered orally. In particular, the present invention relates to an orally administered pharmaceutical composition comprising microparticles of solid fenofibrate that are prepared in the presence of and stabilized by a phospholipid surface active substance according to the process of this invention, wherein a therapeutically effective amount of the composition provides a quantity of fibrate active species to a human patient in need of treatment by the fibrate that is independent of the amount of food taken by the patient.

This invention also relates to an oral dosage form of a pharmaceutical composition comprising a combination of a hydroxymethylglutaryl coenzyme A (HMG-CoA) reductase inhibitor or statin and spray dried microparticles of fenofibrate that are stabilized by a phospholipid surface active substance and a carbohydrate bulking agent prepared according to the process of this invention wherein the dosage form provides to a patient in need of treatment by the statin and fenofibrate a therapeutically effective dose of the statin and a therapeutically effective quantity of fenofibrate active species to said patient when fasted that is at least 80% and especially at least 85% of the quantity of fenofibrate active species, particularly the AUC quantity of fenofibrate active species, provided by said amount to said patient when fed a meal containing fat, especially when fed at least 1000 calories 50% of which are from fat.

It has long been known that the bioavailability of many hydrophobic drugs can be improved if the drugs are administered with food, i.e., the drugs' uptake into the blood or other part of the body exhibit a food effect. A patient is often instructed to take the drug at meal times or with food. Various explanations of the food effect have been advanced including: delayed gastric emptying to allow more drug to dissolve before reaching the small intestine thereby producing longer residence times at specific absorption sites in the small intestine; direct interaction and solubilization of drug by food, especially by hydrophobic food components such as fats and lipids; food-related increases in hepatic blood flow to cause a decrease in first-pass metabolism; and increased gastrointestinal secretions that can improve drug solubility.

Dosage forms or quantities of compositions containing a fibrate such as fenofibrate have been marketed and prescribed for the treatment of dyslipidemia and dyslipoproteinemia. dyslipidemia and dyslipoproteinemia are herein defined to include the group selected from hypercholesterolemia, abnormal and elevated levels of cholesterol, abnormal and elevated levels of LDL cholesterol, abnormal and elevated levels of total cholesterol, abnormal and elevated levels of plasma cholesterol, abnormal and elevated levels of triglycerides, hypertrigylceridaemia, abnormal levels of lipoproteins, abnormal and elevated levels of low density lipoproteins (LDLs), abnormal and elevated levels of very low density lipoproteins, abnormal and elevated levels of very low intermediate density lipoproteins, abnormal levels of high density lipoproteins, hyperlipidemia, hyperchylomicronemia, abnormal levels of chylomicrons, related disorders, and combinations thereof such as those described in The ILIB Lipid Handbook for Clinical Practice, Blood Lipids and Coronary Heart Disease, Second Edition, A. M. Gotto et al, International Lipid Information Bureau, New York, N.Y., 2000, which is hereby incorporated by reference.

Elevation of serum cholesterol, triglyercides, or both is characteristic of hyperlipidemias. Differentiation of specific abnormalities usually requires identification of specific lipoprotein fractions in the serum of a patient. Lipoproteins transport serum lipids and can be identified by their density and electrophoretic mobility. Chylomicrons are among the largest and least dense of the lipoproteins. Others, in order of increasing density and decreasing size include very low density lipoproteins (VLDL or pre-beta), intermediate low density lipoproteins (ILDL or broad-beta), low density lipoproteins (LDL or beta), and high density lipoproteins (HDL or alpha). Triglycerides are transported primarily by chylomicrons and very low density lipoproteins. Cholesterol is transported primarily by low density lipoproteins. Hyperlipidemia types include type I, type IIa, type IIb, type III, type IV, and type V. These types can be characterized according to the levels relative to normal of lipids (cholesterol and triglycerides) and lipoproteins described above. Hyperlipidemia types are listed in Table 1 below, wherein "N" refers to normal levels of the substance in the left column, "+" refers to slightly elevated levels, "++" refers to elevated levels, "−" refers to slightly decreased levels, and "−−" refers to decreased levels, all relative to normal. The data in the table are derived from Drug Facts and Comparisons, 52nd Edition (1998) page 1066. Treatment of a patient presenting one of more of the symptoms listed in Table 1 by the method of treatment and composition of the dosage forms of this invention will lead to a lowering in elevated levels of lipids and lipoproteins in the patient.

TABLE 1

Hyperlipidemia types as a function of relative Lipid and Lipoprotein levels.

| Hyperlipidemia type | I | II a | II b | III | IV | V |
|---|---|---|---|---|---|---|
| Lipids | | | | | | |
| Cholesterol | N+ | ++ | ++ | N++ | N+ | N++ |
| Triglycerides | ++ | N | ++ | N++ | ++ | ++ |
| Lipoproteins | | | | | | |
| Chylomicrons | ++ | N | N | N | N | ++ |
| VLDL (pre-beta) | N+ | N− | ++ | N+ | ++ | ++ |
| ILDL (broad-beta) | | | | ++ | | |
| LDL (beta) | −− | ++ | ++ | ++ | N− | −− |
| HDL (alpha) | −− | N | N | N | N− | −− |

Fibrates used as lipid regulating agents in the treatment of lipid disorders include fenofibrate (brand name TRICOR), bezafibrate (brand name BEZALIP), clofibrate (brand name ATROMID-S), gemfibrozil (brand name LOPID), and ciprofibrate.

Fibrates can act as prodrugs and be metabolized in vivo to provide species that are active species in the treatment of hyperlipidemia. The major metabolite of fenofibrate found in plasma is fenofibric acid, a fibrate active species which has an elimination half-life of approximately twenty hours. Fenofibric acid lowers plasma triglycerides by potentially inhibiting triglyceride synthesis leading to a reduction of VLDL released into the circulation. Fenofibric acid also stimulates the catabolism of triglyceride-rich lipoprotein (VLDL). Measurement of the detected amount of fenofibric acid in the blood of a patient can reflect the efficacy of fenofibrate uptake.

Fenofibrate also reduces serum uric acid levels in hyperuricemic and normal individuals by increasing the urinary excretion of uric acid. The compositions of this invention are also useful in the reduction of uric acid levels.

Fenofibrate or 2-[4-(4-chlorobenzoyl)phenoxy]-2-methyl-propanoic acid 1-methylethyl ester is an example of a poorly water soluble compound. It is a benzophenone containing a para-chlorophenyl group and a para-isopropyloxycarbonylisopropoxyphenyl group, both of which are substantially hydrophobic groups. Fenofibrate exhibits a melting point reported to be in the range of 79 to 82° C. (Physician's Desk Reference, 1999 Edition, page 477), which is above that of the symmetrically unsubstituted benzophenone with a reported melting point range of 48 to 51° C. but below that of the symmetrically substituted 4,4'-dichlorobenzophenone with a reported range of 144 to 146° C. (Aldrich Chemical Co. catalog, 1999).

Fenofibrate acts as a potent lipid modulator agent offering unique and significant clinical advantages over existing products in the fibrate class of drugs. Fenofibrate produces substantial reductions in plasma triglyceride levels in hypertriglyceridemic patients and in plasma cholesterol and LDL-cholesterol in hypercholesterolemic and mixed dyslipidemic patients.

Fenofibrate is a prodrug that is absorbed and then hydrolyzed by tissue and plasma esterases to fenofibric acid, its active metabolite or active species. Fenofibric acid, responsible for the pharmacological activity, has a plasma half-life of about 20 hours. Fenofibrate is a poorly water soluble drug and is practically insoluble in water. It is normally poorly and variably absorbed, and currently is prescribed to be taken with food.

There have been a number of improvements in dosage forms of fenofibrate in an effort to increase bioavailability of the drug and hence its efficacy. However, there is still a need for a dosage formulation that can substantially reduce or overcome the differential between the bioavailability of the drug in patients who are fasted versus the bioavailability of the drug in patients who are fed.

Fenofibrate was first available in a pharmaceutical dosage form (Lipidil®) consisting of a hard gelatin capsule containing fenofibrate, lactose, pregelatinized starch and magnesium stearate. After oral administration, during a meal, about 60% of the dose of this conventional form is effectively absorbed and found in the blood as fenofibric acid (Weil et al., The metabolism and disposition of 14C-fenofibrate in human volunteers, Drug. Metabol. Dispos. Biol. Fate. Chem., 18 (1990) 115–120).

Historically, in order to improve the intestinal absorption, another pharmaceutical dosage form was introduced (Lipidil Micro®). European Patent Application 330,532 and U.S. Pat. No. 4,895,726 disclose a fenofibrate composition in which fenofibrate powder is co-micronized with a solid wetting agent. Sodium lauryl sulfate is described as the wetting agent of choice. The co-micronized powder so obtained is mixed with capsule filling excipients such as lactose, starch, cross-linked polyvinyl pyrrolidone (PVP), and magnesium stearate. A study comparing this formulation (Lipidil Micro®) to the conventional form (Lipidil®) had showed statistically significant increase in bioavailability with the former. A formulation of fenofibrate that refers to this Patent is currently available in the United States under the name TRICOR MICRONIZED®.

European Patent Application 724,877 describes fenofibrate powder co-micronized with a wetting agent in association with a vitamin E component (tocopherol and/or its organic acid ester) for treating or preventing disorders associated with lipoprotein oxidation.

U.S. Pat. No. 4,800,079 describes a medicinal composition in the form of granules with controlled release of fenofibrate. Each granule includes an inert core, a layer based on fenofibrate and a protective layer. Fenofibrate is present in the form of crystalline microparticles of dimensions not greater than 30 μm.

U.S. Pat. No. 4,961,890 describes a process for preparing a controlled release formulation containing fenofibrate in an intermediate layer in the form of crystalline microparticles (less than 30 μm in diameter) within a multilayer layer inert matrix.

European Patent Application 757,911 describes a fenofibrate pharmaceutical dosage form in which fenofibrate is in solution in diethylene glycol monoethyl ether (EMDG) which is a non-ionic surfactant.

European Patent Application No. EP0793958A2 discloses a process for producing a fenofibrate solid dosage form utilizing fenofibrate, a surface active agent and polyvinyl pyrrolidone in which the fenofibrate particles are mixed with a polyvinyl pyrrolidone solution. The thus obtained mixture is granulated with an aqueous solution of one or more surface active agents, and the granulate thus produced is dried.

European Patent Application 904,781 describes a process for making granules of a solid dispersion of a disintegrant in molten fenofibrate by blending a solid dispersing agent into molten fenofibrate, cooling and solidifying the bulk mixture in a tray, and then milling the solid through a screen to produce granules. Disintegrants include polymers such as starch, croscarmellose sodium, sodium starch glycolate, and crospovidone. Such disintegrants are slow to swell and dissolve in aqueous media. Furthermore, when crosslinked as in the case of crospovidone, a polymeric disintegrant will not be uniformly dissolved in molten drug but rather at best will form micro-domains in molten fenofibrate. In addition, polymeric materials can exhibit phase separation phenomena when distributed in a substance with which there is not complete compatibility. This was shown, in part, by Sheu, M. T. et al., "Characterization and dissolution of fenofibrate solid dispersion systems", Int. J. Pharm. (1994), 103(2), 137–46 using differential scanning calorimetry measurements that found fenofibrate to be incompatible with poly (vinyl pyrrolidone). Thus, preparation of a bulk mixture in the melt followed by solidification and grinding can lead to non-uniform distributions and compositions in granules. This can adversely effect the bioavailability of the active component.

U.S. Pat. No. 5,700,471 discloses a process for the micronization of compounds having low solubility in water by exposing such compounds briefly to a temperature above their respective melting points, dispersing them with turbulence in an aqueous or organic phase, and subsequently cooling the phase to form a fine particle dispersion. However, it is specified (column 2, lines 1–9) that certain substances and specifically fenofibrate are not amenable to processing entirely without organic solvents because their aqueous dispersions agglomerate and cannot be metered. Thus, in example 2 of U.S. Pat. No. 5,700,471, fenofibrate is not directly dispersed in water but rather is first dissolved in a four-fold excess of a water-miscible organic solvent (isopropanol) which must be removed in a subsequent step. Organic solvents can pose flammability risks, exposure dangers to process operators, potential environmental problems, and added expense related to their storage, ultimate removal from a formulation, and disposal. Thus it is desirable to overcome the use of organic solvents where possible.

U.S. Pat. No. 4,880,634 describes a method of production of an excipient system containing a pharmacologically active substance for peroral administration comprised of lipid nano-pellets in an aqueous, colloidal suspension. The method comprises forming a melt of a mixture of at least one surfactant, a pharmacologically active substance, and at least one lipid, dispersing the molten mixture within an aqueous solution at a temperature above the melting point of the lipid to form lipid nano-pellets, and cooling the suspension below the melting point of the lipid. In the process, a pharmacologically effective substance is dissolved in the lipid or mixture of lipids during the preparation of the lipid nano-pellets. Animal and plant phospholipids such as lecithin and their hydrogenated forms may be employed in the process although the use of chloroform is taught in examples citing phospholipon 100H. The pharmacologically effective substance can be added to the melted lipid in molten form or dissolved or dispersed in the molten lipid.

U.S. Pat. No. 4,895,726 discloses a gelatin capsule dosage form of fenofibrate containing a co-micronized mixture of particles of fenofibrate and a solid surfactant. The dosage form exhibits improved dissolution rate and bioavailability of fenofibrate over that of micronized fenofibrate alone or that of micronized fenofibrate subsequently mixed with solid surfactant. However, the surfactant must be a solid so it can be micronized, and the micronized surfactant in the form of particles is not uniformly juxtaposed or coated on the surface of the fenofibrate particles.

U.S. Pat. No. 6,180,138 discloses a process for the preparation of solid formulations of a lipid-regulating agent including fenofibrate having enhanced dissolution and absorption characteristics, in which a micronized mixture of the lipid-regulating agent, and optionally one or more excipients, is suspended in a surfactant solution, dried by spray drying, optionally granulated, and optionally converted into a finished capsule or tablet dosage form.

WO 97/13503 discloses a method of synthesizing nanoparticle composites by combining an agent and a matrix to form a composite mixture in an organic solvent or solvent/water, and then spray drying to remove the solvent.

WO 00/40220 discloses a method for making microparticles by dissolving a water insoluble drug in an organic solvent and a water soluble polymer in an organic solvent, mixing the two solutions, and spray drying to obtain microparticles. To increase bioavailability of the drug, the particles are mixed with an oil.

U.S. Pat. No. 5,545,628 discloses a melted and cooled pharmaceutical composition in a hard gelatin capsule for treating hyperlipidemia and/or hypercholesterolemia. The composition contains fenofibrate, one or more polyglycolyzed glycerides, and optionally other polyalkylene glycol polymers that are added to adjust HLB value, melting point, and stability. The composition provides an increased bioavailability of fenofibrate with respect to previously marketed forms of fenofibrate (i.e., non co-micronized Lypantyl 200 RTM., and co-micronized Lypantyl 200 M.RTM.). Commercially available formulations of fenofibrate such as TRICOR Micronized exhibit a food effect, for example, the amount of fenofibrate taken up and metabolized to the active fibrate species, fenofibric acid, depends on the amount and kind of food taken proximal (within about +/− one or two hours before or after) the time of taking the fenofibrate oral dosage form (e.g., capsule or tablet).

Ben-Armor solubilized fenofibrate in nonaqueous dimethyl isosorbide with a miscible wetting agent to improve its bioavailability. Colloidal silicon oxide was added to increase the viscosity, and the liquid so obtained was placed in hard gelatin capsules and sealed. In vivo studies with this formulation indicated no statistically significant difference in bioavailability between the liquid formulation and a conventional form when the product was given with food.

U.S. Pat. Nos. 5,645,856 and 6,096,338 disclose a composition and method of improving the in vivo bioavailability of a hydrophobic drug from a pharmaceutical composition comprising the drug dispersed or dissolved in a digestible oil containing a hydrophilic surfactant which substantially inhibits the in vivo lipolysis of the digestible oil, wherein there is added to the composition a lipophilic surfactant capable of reducing the inhibitory effect of the hydrophilic surfactant. They also disclose a carrier system for a hydrophobic drug which comprises a digestible oil and a pharmaceutically acceptable surfactant for dispersing the oil in vivo upon administration of the carrier system, the surfactant comprising a hydrophilic surfactant component which substantially inhibits the in vivo lipolysis of the digestible oil, and a lipophilic surfactant component capable of reducing the inhibitory effect of the hydrophilic surfactant component.

U.S. Pat. Nos. 5,776,495 and 6,027,747 disclose a solid dispersion with enhanced bioavailability of a surface active agent and at least one therapeutic agent in a hydrophilic carrier having enhanced solubility in an aqueous medium. The dispersion is prepared by dissolving the therapeutic agent in a volatile organic solvent containing a very hydrophilic polymer and without strong heat or vacuum evaporating the solvent to dryness to form a co-precipitate of therapeutic agent and hydrophilic polymer.

U.S. Pat. No. 5,827,536 discloses soluble fenofibrate pharmaceutical dosage formulations exhibiting improved bioavailability after oral administration. However, the formulations contain fenofibrate as a solution in a solubilizing agent consisting of diethylene glycol monoethyl ether.

U.S. Pat. No. 6,042,847 discloses a three-phase pharmaceutical form exhibiting constant and controlled release of an amorphous active ingredient stabilized with polymers for a single daily peroral application. The first phase consists of a core containing an amorphous active ingredient, polyvinylpyrrolidone and a cellulose ether as carriers and as inhibitors of its crystallization, and a surfactant that improves the solubility of the active ingredient and promotes the absorption of the amorphous active ingredient from gastrointestinal tract. The second phase contains a cellulose ether and a mixture of mono-, di- and triglycerides as sustained release agents. The third phase is a poorly soluble or gastro-resistant polymeric film coating.

U.S. Pat. No. 6,068,854 discloses a constant release tablet consisting of a matrix of gelatin in which is dispersed as an emulsion, dispersion or colloid a lipophilic and/or poorly water soluble pharmaceutical substance with a particle size below 200 micrometers.

WO 2000037057 discloses a solution formulation comprising a lipid-regulating agent dissolved in at least one propylene glycol fatty acid ester as the primary solvent medium for the agent, optionally together with one or more emulsifiers including phospholipids.

WO 2000016749 discloses a formulation comprising a solution of a lipid-regulating agent dissolved in at least one propylene glycol fatty acid ester as the primary solvent medium for the agent. One or more emulsifiers may be added to the formulation.

WO 98/31361 discloses a pharmaceutical composition of fenofibrate with high biological availability and method for preparing same. The invention concerns a fenofibrate composition with instant release comprising and inert water-soluble support coated with at least a film containing an active fenofibrate principle in micronized form with a size less than 20 micrometers, a hydrophilic polymer and optionally a surfactant, and optionally one or several external phases or films.

U.S. Pat. No. 5,880,148 discloses a combination of fenofibrate and a vitamin E substance where the fenofibrate is micronized with a solid surfactant.

U.S. Pat. No. 6,074,670 discloses an immediate-release fenofibrate composition comprising an inert hydrosoluble carrier covered with a layer containing fenofibrate in a micronized form having a size less than 20 micrometers, a hydrophilic polymer and, optionally, a surfactant. In an example cited, a suspension of micronized fenofibrate and sodium lauryl sulfate is suspended in a solution of sodium lauryl sulfate and polyvinylpyrrolidone, sprayed onto 100 to 400 micrometers size lactose particles suspended in a fluidized air bed granulator, and the granulate is placed in capsules or transformed into tablets by mixing with cross-linked PVP, microcrystalline cellulose, colloidal silica, and sodium stearyl fumarate. The composition showed enhanced bioavailability of fenofibrate. However, increased dissolution rates of a formulation of fenofibrate do not translate directly or linearly to increase uptake of the drug, and show that an in vitro experimental result can not necessarily predict the results of an in vivo experiment.

It is generally accepted that water insoluble or poorly water soluble drugs can be made more bioavailable when presented in the form of small particles. In many cases, it is known that small particles must be stabilized against particle size growth and agglomeration by the addition of one or more surface active agents at some point in the preparation of the particles, especially in a size reduction process that employs the input of mechanical energy such as homogenization, microfluidization, milling, such as media milling, precipitation such as from a liquefied gas, ball milling and the like. Because they are biocompatible and well tolerated in vivo, preferred surface active agents or particle stabilizers are phospholipids, and preferred small particles of fenofibrate are stabilized by phospholipid particle stabilizers that are also referred to herein as phospholipid surface active substances or species. A phospholipid surface active substance can be a single phospholipid compound or a mixture of phospholipid compounds, a natural phospholipid isolated for example from plants such as soy or animal sources such as hen egg, or a synthetic phospholipid. Phospholipids that are isolated from plants or animals can be purified into different grades of phospholipids including grades sold for use in food and grades sold for use in pharmaceuticals. For example, Lipoid E 80 may contain phosphatidyl choline, phosphatidyl ethanolamine, lysophosphatidyl choline, lysophosphatidyl ethanolamine, sphingomyelin, and trace quantities of triglycerides, cholesterol, free fatty acids, d,l-alpha-tocopherol, and water.

Microparticles of water insoluble or poorly soluble substances are small particles having diameters of from nanometers to micrometers and refer to solid particles of irregular, non-spherical or spherical shapes. When the insoluble and poorly soluble substances are therapeutically and diagnostically useful substances, formulations containing them as microparticles or small particles provide some specific advantages over unformulated non-micronized drug particles. These advantages include improved oral bioavailability of drugs that are poorly absorbed from the GI tract, development of injectable formulations that are currently available only in oral dosage form, less toxic injectable formulations that are currently prepared with organic solvents, sustained release of intramuscular injectable drugs that are currently administered through daily injection or constant infusion, preparation of inhaled and ophthalmic formulations of drugs that otherwise could not be formulated for nasal or ocular use, as well as other advantages.

Current technology for delivering insoluble drugs as described in U.S. Pat. Nos. 5,091,188; 5,091,187 and 4,725,442 focuses on (a) either coating small drug particles with surface active substances that are natural or synthetic phospholipids or (b) dissolving the drug in a suitable lipophilic carrier and forming an emulsion stabilized with surface active substances that are natural or semisynthetic phospholipids.

U.S. Pat. No. 5,145,684 discloses methods for preparation and dispersions of particles consisting of crystalline drug substance having a surface modifier or surface active substance adsorbed to maintain an effective average particle size of less than about 400 nm. However, the method requires a milling step that can result in impurities being added to the formulation from fractured milling media.

U.S. Pat. Nos. 5,470,583 and 5,336,507 disclose methods for preparation of nanoparticles using a charged phospholipid as a cloud point modifier.

U.S. Pat. No. 5,302,401 discloses nanoparticles having a surface modifier adsorbed on the surface of the particles and a cryoprotectant associated therewith. The cryoprotectant is present in an amount sufficient to allow the nanoparticles to be lyophilized.

International Patent Application WO 99/39700 describes the preparation of submicron nanoparticles from a pharmacologically active principle and a composite material consisting of at least one lipidic substance and at least one amphiphilic substance using high pressure homogenization to form a microemulsion of the composite material at a temperature higher than the melting temperature of at least one of the materials forming the composite and in the presence of one or more aqueous surfactants as surface active substances and then cooling the microemulsion to form a dispersion of solid particles.

U.S. Pat. No. 5,785,976 discloses a heated aqueous emulsification and cooling process for the preparation of solid lipid particles. In that process a solid lipid or bioactive agent or a mixture of solid lipids or bioactive agents is melted and stabilizers, i.e., surface active substances, are added either to the lipid or bioactive agent and to the aqueous phase or to the aqueous phase only. The aqueous phase is heated to the temperature of the melt before mixing and may contain stabilizers, isotonicity agents, buffering substances, cryoprotectants and/or preservatives. The molten lipid compounds and the bioactive agents can be emulsified in the aqueous phase by high-pressure homogenization. The homogenized dispersion is then allowed to cool until solid particles are formed by recrystallization of the dispersed agents. Drugs or other bioactive substances to be incorporated into the particles may be melted together with the lipids or may be dissolved, solubilized or dispersed in the lipid melt before an emulsification by homogenization step.

U.S. Pat. No. 5,922,355 discloses a method for preparing submicron size microparticles by particle size reduction methods in which a solid material is reduced in size over a period of time while continuously below the melting point of the material or by precipitation while the particles are stabilized with phospholipids as surface active substances in combination with other surface modifiers to control growth of particle size and enhance storage stability. The use of one or more surface modifiers in addition to a phospholipid provides volume weighted mean particle size values that are much smaller than what can be achieved using phospholipid alone without the use of an additional surface active substance (surfactant) with the same energy input while providing compositions resistant to particle size growth on storage. The phospholipid and the surfactant are both present at the time of particle size reduction.

WO 00/30616 discloses a rapidly dispersing solid dry dosage form comprised of a water insoluble compound existing as a nanometer or micrometer particulate solid which is surface stabilized by the presence of at least one phospholipid, the particulate solid being dispersed throughout a bulking matrix. When the dosage form is introduced into an aqueous environment, the bulking matrix is substantially completely dissolved within less than 2 minutes thereby releasing the water insoluble particulate solid in an unaggregated and/or unagglomerated state. The matrix is composed of a water insoluble substance or therapeutically useful water insoluble or poorly water soluble compound, a phospholipid and optionally also at least one non-ionic, anionic, cationic, or amphiphatic surfactant, together with a matrix or bulking agent and if needed a release agent. The volume weighted mean particle size of the water insoluble particle is 5 micrometers or less.

In humans, cholesterol and triglycerides (TG) are part of lipoprotein complexes in the bloodstream, and can be separated via ultracentrifugation into high-density lipoprotein (HDL), intermediate-density lipoprotein (IDL), low-density lipoprotein (LDL) and very-low-density lipoprotein (VLDL) fractions. Cholesterol and triglycerides are synthesized in the liver, incorporated into VLDL, and released into the plasma. High levels of total cholesterol (total-C), LDL-C, and apolipoprotein B (apo-B, a membrane complex for LDL-C) promote human atherosclerosis, and decreased levels of HDL-C and its transport complex, apolipoprotein A, are associated with the development of atherosclerosis. Cardiovascular morbidity and mortality in humans can vary directly with the level of total-C and LDL-C and inversely with the level of HDL-C.

Orally administered statins are hydroxymethylglutaryl coenzyme A (HMG-CoA) reductase inhibitors that are used in patients to lower low density lipoprotein (LDL) cholesterol. Complimentary to this are orally administered fibrates which are used in patients to decrease lipoproteins rich in triglycerides, to increase high density lipoprotein (HDL), and to decrease atherogenic-dense LDL. Patients who take statins or fibrates are frequently on diets with low and variable fat content.

Uptake of a fibrate such as fenofibrate by a patient is sensitive to a positive food effect, hereinafter referred to simply as a food effect. A positive food effect (or food effect) exits when the amount of an active drug taken into the blood from a given oral dosage form by a fasting patient is less than the amount of the active drug taken into the blood from the same dosage form by the same patient who has eaten a fat-containing meal proximal to the time of administration of the dosage form. A negative food effect exits when the amount of an active drug taken into the blood from a given oral dosage form by a fasting patient is more than the amount of the active drug taken into the blood from the same dosage form by the same patient who has eaten a fat-containing meal proximal to the time of administration of the dosage form. The compositions of this invention generally exhibit a positive food effect.

Patients with severe primary hypercholesterolemia often present with blood levels of low density lipoprotein (LDL) cholesterol greater than 190 mg/dl (4.9 mmol/L) and triglyceride levels up to 350 mg/dl (3.9 mmol/L). The use of diet and single-drug therapy does not always decrease LDL cholesterol and triglycerides adequately enough to reach targeted values in patients with primary severe hypercholesterolemia with or without a concomitant increase in triglycerides. In these patients a combination of complementary fibrate therapy and statin therapy can be desirable.

HMG-CoA reductase (3-hydroxy-3-methylglutaryl-coenzyme A) is the microsomal enzyme that catalyzes the rate limiting reaction in cholesterol biosynthesis (Mevalonate). A statin compound is an HMG-CoA reductase inhibitor that inhibits HMG-CoA reductase, and therefore inhibits or interferes with the synthesis of cholesterol. Inhibition of cholesterol synthesis can lead to a reduction in blood cholesterol levels.

A large number of naturally or synthetically obtained or synthetically modified compounds have been found to inhibit HMG-CoA reductase. These compounds form a category of agents useful for practicing the present invention. Traditionally these agents have been used to treat individuals with hypercholesterolemia. Examples include statins, which are commercially available, such as lovastatin and mevinolin disclosed in U.S. Pat. No. 4,231,938, pravastatin and pravastatin sodium disclosed in U.S. Pat. No. 4,346,227, fluvastatin and fluvastatin sodium and XU 62-320 disclosed in EP 0 114 027 and U.S. Pat. No. 4,739,073, atorvastatin disclosed in U.S. Pat. No. 5,273,995, itavastatin also known as NK-104 disclosed in EP304063, mevastatin disclosed in U.S. Pat. No. 3,983,140, rosuvastatin, velostatin and synvinolin and simvastatin disclosed in U.S. Pat. Nos. 4,448,784 and 4,450,171, cerivastatin and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624, RE36,520, and 4,897,402, the disclosures of which patents are incorporated herein by reference.

Lovastatin, an inactive lactone, is a white, nonhygroscopic crystalline powder isolated from a strain of *Aspergillus terreus* that is insoluble in water and sparingly soluble in ethanol, methanol, and acetonitrile. Lovastatin is hydrolyzed after oral ingestion to the corresponding (beta)-hydroxyacid. This metabolite is an inhibitor of 3-hydroxy-3-methylglutaryl-coenzyme A (HMG-CoA) reductase. When formulated for oral administration as Mevacor, tablets can contain a therapeutically effect dose range of 10 to 40 mg of lovastatin together with pharmaceutically acceptable excipients such as cellulose, lactose, magnesium stearate, starch, and butylated hydroxyanisole as a preservative. When taken separately, lovastatin can treat related hyperlipidemia such as reduce plasma total-C, LDL-C, total-C/HDL-C ratio and LDL-C/HDL-C ratio as well as increase HDL-C, and modestly decrease VLDL-C and plasma triglycerides TG. Mevacor can lower total-C and LDL-C to target levels, and reduce elevated total-C and LDL-C levels in patients with primary hypercholesterolemia (Types IIa and IIb). Single daily doses given in the evening can be more effective than the same dose given in the morning, perhaps because cholesterol is synthesized mainly at night. A recommended starting dose of Mevacor is preferably given with a meal. 20 mg once a day can be given with the evening meal. Storage between 5–30° C. (41–86° F.) is preferred.

Fluvastatin (also known as fluvastatin sodium), a synthetic HMG-CoA reductase inhibitor, is a white to pale yellow, hygroscopic powder soluble in water, ethanol and methanol. When formulated for oral administration as Lescol®, capsules can contain a therapeutically effect dose range of 20 to 40 mg of fluvastatin together with pharmaceutically acceptable excipients such as gelatin, magnesium stearate, microcrystalline cellulose, pregelatinized starch, red iron oxide, sodium lauryl sulfate, talc, titanium dioxide, yellow iron oxide, and other ingredients. Fluvastatin sodium reduces Total-C, LDL-C, and apolipoprotein B, and moderately reduces triglycerides (TG) while producing an increase in HDL-C of variable magnitude. Following oral administration, fluvastatin is absorbed rapidly and completely with peak concentrations reached in less than 1 hour. Administration with food reduces the rate but not the extent of absorption. Fluvastatin sodium is indicated as an adjunct to diet in the treatment of elevated total cholesterol (Total-C), LDL-C. TG and Apo B levels in patients with primary hypercholesterolemia and mixed dyslipidemia (Frederickson Type IIa and IIb). It is also indicated to slow the progression of coronary atherosclerosis in patients with coronary heart disease as part of a treatment strategy to lower total and LDL cholesterol to target levels.

Atorvastatin (or Atorvastatin calcium 2:1) is a white to off-white crystalline trihydrate powder that is insoluble in aqueous solutions of pH 4 and below, and is very slightly soluble in distilled water, pH 7.4 phosphate buffer, and acetonitrile, slightly soluble in ethanol, and freely soluble in methanol. When formulated in Lipitor® tablets for oral administration, tablets can contain a therapeutically effect dose range of 10 to 80 mg of atorvastatin as well as pharmaceutically acceptable excipients such as calcium carbonate, USP; candelilla wax, FCC; croscarmellose sodium, NF; hydroxypropyl cellulose, NF; lactose monohydrate, NF; magnesium stearate, NF; microcrystalline cellulose, NF; Opadry White YS-1-7040 (hydroxypropylmethylcellulose, polyethylene glycol, talc, titanium dioxide); polysorbate 80, NF; and simethicone emulsion. Atorvastatin can reduce total-C, LDL-C, and apo B in patients with homozygous and heterozygous familial hypercholesterolemia, nonfamilial forms of hypercholesterolemia, and mixed dyslipidemia. Atorvastatin can also reduce VLDL-C and TG and produces variable increases in HDL-C and apolipoprotein A-1. Atorvastatin can reduce total-C, LDL-C, VLDL-C, apo B, TG, and non-HDL-C, and can increase HDL-C in patients with isolated hypertriglyceridemia. Atorvastatin can reduce intermediate density lipoprotein cholesterol (IDL-C) in patients with dysbetalipoproteinemia. Food decreases the rate and extent of drug absorption as assessed by $C_{max}$ and AUC, but LDL-C reduction is similar whether atorvastatin is given with or without food. Atorvastatin can be administered as a single dose at any time of the day, with or without food. Atorvastatin can reduce total-C, LDL-C, VLDL-C, apo B, and TG, and can increase HDL-C in patients with hypercholesterolemia and mixed dyslipidemia.

Simvastatin is a white to off-white, nonhygroscopic, crystalline powder that is practically insoluble in water, and freely soluble in chloroform, methanol and ethanol. Simvastatin is derived synthetically from a fermentation product of *Aspergillus terreus*. After oral ingestion, simvastatin, which is an inactive lactone, is hydrolyzed to the corresponding (beta)-hydroxyacid form which is an inhibitor of 3-hydroxy-3-methyl-glutaryl-coenzyme A (HMG-CoA) reductase. When formulated as Zocor for oral administration, tablets can contain a therapeutically effect dose range of 5 mg to 80 mg of simvastatin as well as pharmaceutically acceptable excipients cellulose, hydroxypropyl cellulose, hydroxypropyl methylcellulose, iron oxides, lactose, magnesium stearate, starch, talc, titanium dioxide as well as other ingredients including butylated hydroxyanisole which can be added as a preservative. Simvastatin shows no fed-fasted effect when administered immediately before a low-fat meal. Simvastatin can reduce total-C, LDL-C, total-C/HDL-C ratio, and LDL-C/HDL-C ratio as well as decrease TG and increase HDL-C.

Cerivastatin (or Cerivastatin sodium) is a white to off-white hygroscopic amorphous powder that is soluble in water, methanol, and ethanol, and very slightly soluble in acetone. Cerivastatin sodium is a synthetic, enantiomerically pure competitive inhibitor of the enzyme 3-hydroxy-3-methylglutaryl-coenzyme A (HMG-CoA) reductase that catalyzes the conversion of HMG-CoA to mevalonate in an early and rate-limiting step in the biosynthesis of cholesterol. The inhibition of cholesterol biosynthesis reduces the level of cholesterol in hepatic cells which stimulates the synthesis of LDL receptors and increases the uptake of cellular LDL particles. This can lead to a reduction in plasma cholesterol concentration. When formulated as Baycol®, cerivastatin sodium tablets can contain a therapeutically effect dose range of 0.2 to 0.8 mg of cerivastatin sodium for oral administration and can be taken with or without food. Other tablet ingredients can include pharmaceutically acceptable excipients such as mannitol, magnesium stearate, sodium hydroxide, crospovidone, povidone, iron oxide yellow, methylhydroxypropylcellulose, polyethylene glycol, and titanium dioxide. In patients with hypercholesterolemia, cerivastatin sodium can produce reduced levels of plasma total cholesterol, LDL-C, and apolipoprotein B, VLDL-C and plasma triglycerides and increases plasma HDL-C and apolipoprotein A-1. Cerivastatin systemic exposure (area under the curve, AUC) and $C_{max}$ are not sensitive to a food effect, but once daily doses of 0.2 mg can be more efficacious than twice daily doses of 0.1 mg. Cerivastatin sodium can be effective as an adjunct to diet to reduce elevated Total-C, LDL-C, apo B, and TG and to increase HDL-C levels in patients with primary hypercholesterolemia and mixed dyslipidemia (Fredrickson Types IIa and IIb) when the response to dietary restriction of saturated fat and cholesterol and other non-pharmacological measures alone is inadequate.

Pravastatin (or pravastatin sodium) is a white to off-white, fine or crystalline powder. It is a relatively polar hydrophilic compound with a partition coefficient (octanol/water) of 0.59 at a pH of 7.0. It is soluble in methanol and water (>300 mg/mL), slightly soluble in isopropanol, and practically insoluble in acetone, acetonitrile, chloroform, and ether. When formulated as Pravachol for oral administration, tablets can contain a therapeutically effect dose range of 10 to 40 mg of pravastatin. Inactive ingredients can include pharmaceutically acceptable excipients such as croscarmellose sodium, lactose, magnesium oxide, magnesium stearate, microcrystalline cellulose, and povidone. A 10 mg tablet can also contain Red Ferric Oxide, a 20 mg tablet can also contain Yellow Ferric Oxide, and a 40 mg tablet can also contain Green Lake Blend (mixture of D&C Yellow No. 10-Aluminum Lake and FD&C Blue No. 1-Aluminum Lake).

Itavastatin is an inhibitor of HMG-CoA reductase and can be dosed in tablets containing a therapeutically effect dose range from about 1 mg to about 20 mg, preferably from about 2 mg to about 10 mg.

Rosuvastatin is an inhibitor of HMG-CoA reductase and can be dosed in tablets containing a therapeutically effect dose range from about 4 or 5 mg to about 10 or 20 mg, with reported doses of up to about 80 mg per day when formulated as Crestor.

Preferred statins in this invention are those useful for oral administration. Most preferred statins in this invention include lovastatin, pravastatin, simvastatin, atorvastatin, rosuvastatin, fluvastatin, itavastatin and cerivastatin.

Combination of a statin with a fibrate has been shown to produce beneficial effect in the treatment of hyperlipidemia and hyperlipoproteinemia. However, the fibrates used previously have a limitation related to the presence of a food effect and require patient restrictions and relatively higher dosage amounts of each drug. Surprisingly, the compositions of this invention comprising a fibrate, more specifically fenofibrate, together with a statin are substantially devoid of food effect, particularly with respect to the uptake of the fibrate.

Raza, et al. in WO 0045817 disclosed safe non-interacting drug combinations of a 3-hydroxy-3-methylglutaryl CoA (HMG-CoA) reductase inhibitor and a drug that is either an inducer, inhibitor, or substrate of cytochrome P 450. Particular combinations are useful in treating hyperlipidemia in humans who are receiving immunosuppressive chemotherapy. A preferred combination is the agent and a fibrate drug, the use of such a combination in treating hyperlipidemia in mammals, and medicaments containing such a combination for use in such treatments. Lipantil™, a brand of fenofibrate used is known to have food effects Pan et al. in J. Clin. Pharmacol. (2000), 40(3), 316–323 reported that concomitant administration of fenofibrate and pravastatin did not affect the pharmacokinetics of either fenofibric acid or pravastatin in healthy adult volunteers who received single doses of 201 mg fenofibrate alone, 201 mg fenofibrate +40 mg pravastatin, and 40 mg pravastatin alone. However, the combination of fenofibrate and pravastatin was administered as sepalate dosage forms, and uptake of fenofibrate is subject to a food effect.

Farnier, M. and Dejager, S. in Am. J. Cardiol. (2000), 85(1), 53–57 reported that the addition of fluvastatin to micronized fenofibrate results in substantial improvement in atherogenic plasma lipids levels in severe primary hypercholesterolemia and is well tolerated. Patients received micronized fenofibrate 200 mg, fluvastatin 20 mg plus micronized fenofibrate 200 mg, or fluvastatin 40 mg plus micronized fenofibrate 200 mg. However, the fenofibrate and the statin were administered in separate dosage forms, and uptake of micronized fenofibrate demonstrates a food effect.

Kayikcioglu et al. in Am. J. Cardiol. (1999), 83(7), 1135–1137 reported that simvastatin 10 mg administered on alternate days with fenofibrate 250 mg is as effective as a daily dose of simvastatin 10 mg and fenofibrate 250 mg in lowering plasma cholesterol, triglycerides, and LDL cholesterol, and increasing HDL cholesterol levels in patients with mixed hyperlipidemia. The fenofibrate and simvastatin were administered in separate dosage forms and uptake of fenofibrate is subject to a food effect.

EP 0 475 148 A1 discloses that tablets containing pravastatin in combination with tablets of a fibric acid derivative were useful for prevention or treatment of type III hyperlipoproteinemia.

EP 0 455 042 A1 discloses a combination of pravastatin and fenofibrate in a single capsule for the treatment of dyslipidemia. However, the combination is prepared by grinding a tablet of pravastatin and a tablet of fenofibrate to a powder for use in a single capsule, and this form of fenofibrate exhibits a food effect.

Ippen et al in WO 0037078 describe a combination of the 3-hydroxy-3-methylglutaryl-coenzyme A inhibitor, cerivastatin with fenofibrate and to its use in the prophylaxis and treatment of disorders and diseases of lipid metabolism. The tablets containing the two actives are prepared by standard wet granulation. Such forms of fenofibrate exhibit a food effect.

Canadian Patent 2,048,395 provides a method for preventing or treating type III hyperlipoproteinemia by administering pravastatin alone or in combination with a fibric acid derivative such as fenofibrate. Tablets containing pravastatin and fenofibrate alone or in combined were prepared by standard dry granulation method using fenofibrate that is subject to food effect.

Statins are subject to substantial first pass metabolism in the liver where they inhibit HMG-CoA reductase to reduce production of cholesterol. Efficacies of statins are not substantially reduced by the presence or absence of food.

While blood levels of active drug or active species from an oral dose of a fibrate such as fenofibrate in a patient are susceptible to a food effect (i.e., variable uptake between fed and fasted states) leading to variation in the amount of active drug species received from a given dose of a fibrate, the efficacy of most statins is not substantially compromised by the presence or absence of food. In a combination dosage form of a statin and a fibrate such as fenofibrate, intake or absence of intake of food can lead to unexpectedly high or low levels of the active fibrate in the presence of a given dosage level of a statin. This lack of control of fibrate level in the blood can potentially lead to undesired side effects such as myopathy and rhabdomyolysis that have sometimes been seen previously with statins alone and with fibrates and statins when administered concurrently to a patient, particularly as a result of concurrent administration of gemfibrozil and lovastatin. Administration of separate dosage forms of a statin and of a fibrate can also pose the potential for variable uptake of either drug, for example when a patient overdoses or underdoses one or the other individual dosage form by taking more or fewer doses of either separate drug than the patient's condition would require for treatment. This can happen when a patient forgets to take one or the other drug dosage form, or when the patient forgets that he or she has taken one or the other drug dosage form and subsequently takes a second or even a third or more dosage form of one or both of the drugs. This can be especially prevalent in an older patient and in a patient with a failing memory.

Thus there is a need for a single therapeutically effective oral dosage form comprising a combination of a hydroxymethylglutaryl coenzyme A (HMG-CoA) reductase inhibitor (or a statin) and a fibrate that provides adequate delivery of both a therapeutically effective amount the HMG-CoA reductase inhibitor (statin) and a therapeutically effective amount of the fibrate active species without substantial variability in the amounts of either of the drugs received in a patient between a fasted and fed states. It is an object of this invention to provide such a dosage form.

In this regard, this invention provides a novel pharmaceutical composition comprising a combination of a hydroxymethylglutaryl coenzyme A reductase inhibitor and a fibrate, particularly fenofibrate, in the form of microparticles of solid fibrate that are stabilized by phospholipid as a surface active substance and that provide reduced in vivo variability in the therapeutically effective amounts of either of the drugs in a patient between a fed and fasted states when administered orally. The present invention further provides novel pharmaceutical compositions comprising a combination of a statin and a fibrate, particularly fenofibrate, in the form of microparticles of solid fibrate that are stabilized by phospholipid as a surface active substance and that provide reduced in vivo variability in the bioavailability of the drug among fed and fasted patients when administered orally.

In particular, the present invention provides a dosage form such as an orally administered dosage form of a pharmaceutical composition comprising a combination of a statin and microparticles of fenofibrate that are spray dried from a molten heated homogenate of microparticles of fenofibrate that are stabilized by a phospholipid surface active substance in the presence of a bulking agent, wherein the dosage form provides to a patient in need of treatment by the combination of statin and fenofibrate a therapeutically effective dose of the statin and a therapeutically effective quantity of fenofibrate active species to said patient when fasted that is at least 80% of the quantity of fenofibrate active species provided by said amount to said patient when fed a meal containing fat.

In one aspect while it is advantageous in very many cases to use particulate pharmaceutical formulations wherein particle sizes are stabilized by combinations of phospholipids and surface modifiers according to U.S. Pat. No. 5,922,355, it is sometimes desirable to produce pharmaceutical formulations or pre-formulations which are stabilized by biocompatible phospholipids without the use of additional surface active substances. This can be desirable, for example, when there is a subsequent need to modify the composition of a particle-containing formulation in a step following the formation of the particles such as by the addition of one or more additional ingredients that are not compatible with additional surface modifiers shown to be beneficial in U.S. Pat. No. 5,922,355, the disclosure of which is hereby incorporated by reference. In one aspect it is therefore desirable to produce drug particles stabilized by one or more phospholipids in the absence of additional surface modifiers but which exhibit enhanced stability toward particle growth and which maintain sub-micron and micron size particles on subsequent storage as suspension or solid dosage form.

In another aspect, particle size reduction methods such as those disclosed in U.S. Pat. No. 5,922,355 in which particles of a material are reduced in size in the presence of phospholipid and another surface active substance while the material is maintained in the solid phase require processing for a certain length of time to achieve a desired particle size. The time is directly related to the number of homogenization volume passes or turnovers performed on a volume of a suspension of particles in a size reduction process. It is desirable to further reduce that length of time by providing an improved process that can decrease the overall number of turnovers to achieve a desired particle size.

While these disclosures provide compositions and methods to enhance the bioavailability of fibrates such as fenofibrate from various dosage forms, none sufficiently address the need to substantially reduce or eliminate the difference between the amount of the drug taken up in patients who are fasting versus the otherwise enhanced uptake of the drug in patients who are fed or take food with or proximal to the taking of a dosage form of a fibrate.

D. Fleischer, Cheng Li, Yuji Zhou, Li-Heng Pao and Aziz Karim in "Drug, Meal and Formulation Interactions Influencing Drug Absorption After Oral Administration," Clin. Pharmacokinet. (1999), Mar:36 (3), 233–264 review information regarding oral drug/meal interaction effects on GI drug absorption.

It is thus an object of this invention to provide to a mammal such as a human patient compositions and a method of treatment of dyslipidemia and dyslipoproteinemia and related disorders in the patient comprising administration of an oral pharmaceutical dosage form of a fibrate such as fenofibrate that substantially reduces or substantially eliminates the difference in the amount of the drug or active fibrate species taken up in the patient when in a fasting state versus the amount taken up using the same dosage level in the same patient when in a fed state.

It is another object of this invention to provide a composition of a pharmaceutical dosage form of a fibrate such as fenofibrate that substantially reduces the difference between the amount of the drug taken up in a patient who is fasting versus the amount of the drug take up in the same patient who is fed.

It is another object of this invention to provide a pharmaceutical dosage form of a fibrate such as fenofibrate in a capsule or a tablet form that can be administered to provide substantial reduction or elimination of an effect of food on the uptake of the fibrate into the patient, i.e., substantial reduction or elimination of the food effect.

It is another object of this invention to provide a once-a-day pharmaceutically effective dosage form of a fibrate such as fenofibrate that can be administered to a patient in need of treatment by the drug.

BRIEF SUMMARY OF THE INVENTION

The present invention describes a process for the preparation of dried small particles of fenofibrate stabilized by phospholipid comprising the steps of (a) mixing in an aqueous carrier in the absence of an organic solvent at high shear and within a first temperature range at or above the melting point of the fenofibrate an admixture of fenofibrate and one or more than one surface active substance of which at least one is a phospholipid, and optionally one or more bulking agents, to form a heated suspension containing the drug, then (b) homogenizing said heated suspension in a first pressure range and within said first temperature range to form a heated homogenate containing the drug, optionally with the addition of one or more bulking agents at some time before, during or after the homogenization, then (c) spray drying the heated homogenate to form a dried composition of bulking agent and small particles containing the fenofibrate.

In a typical procedure, a premix of fenofibrate, phospholipid Lipoid E80 (dispensed frozen but liquefied or vesiclized at processing temperatures), a bulking agent such as a carbohydrate (e.g., mannitol, sucrose, sucrose plus raffinose, lactose and the like) in 10 millimolar aqueous phosphate buffer at pH 8 is microfluidized above the melting temperature of fenofibrate for about 3 to 10 volume passes and then spray dried.

The homogenization step is done on a heated suspension having the fenofibrate in a molten phase in the presence of one or more than one surface active substance at least one of which is a phospholipid to provide a heated homogenate containing the drug. The heated homogenate can be in the form of a microemulsion comprising small molten particles or droplets of drug stabilized by a phospholipid and optionally one or more than one surface active substance. The heated homogenate containing the drug is then spray dried to form a dried solid as a powder that comprises small particles of drug in which the drug is in a solid phase. The solid fenofibrate may be amorphous, it may be crystalline, or it may be a combination of both amorphous and crystalline. The small particles are stabilized against particle size growth and agglomeration in the molten phase by the phospholipid surface active substance or substances in the presence of a bulking agent.

The phospholipid is in a hydrated, molten or dispersed state during the particle size reduction homogenization step.

Unlike the process of End et al. in U.S. Pat. No. 5,700, 471, the spray drying of molten fenofibrate particles can be done without organic solvent, without significant growth of particle size of the fenofibrate particles, and without precipitation or unwanted phase separation of the fenofibrate as large crystals. The spray drying of the molten fenofibrate provides small particles or microparticles of fenofibrate stabilized by phospholipid. The process prevents relatively large crystals and/or agglomerates of the poorly water soluble drug from forming. The process provides a means of overall rapid formation of large quantities of desired dried small particles containing the poorly water soluble drug, fenofibrate.

By "dried" we mean having a water or moisture content greater than zero percent and below 5% by weight, preferably below 4% by weight, more preferably below 3% by weight, and even more preferably below 2% by weight, and most preferably below 1% by weight. In preferred embodiments, the amount of water is between 0.1% and 3%, more preferably between 0.1% and 2%, and most preferably between 0.1% and 1% by weight. By "anhydrous" we mean have zero water content.

It is an advantage of this invention that small particles containing a fenofibrate can be prepared in the absence of an organic solvent.

It is another advantage of this invention that small particles containing a poorly water soluble drug, fenofibrate, can be prepared using pharmaceutically acceptable excipients such as phospholipids, carbohydrates such as sugars and other polyols.

It is a further advantage of this invention that a composition of a pharmaceutical dosage form of fenofibrate is provided that substantially reduces the difference between the amount of the drug taken up in patients who are fasting versus the amount of the drug in patients who are fed.

It is yet another advantage of this invention that a pharmaceutical dosage form of fenofibrate is provided that can be administered orally in a capsule or a tablet or a powder form.

It is still another advantage of this invention that a once-a-day pharmaceutically effective dosage form of fenofibrate is provided that can be administered orally to a patient in need of treatment by the drug without regard to the amount of food a patient has ingested prior to or following administration of the dosage form. These and other advantages will be readily apparent from the description of the invention.

DETAILED DESCRIPTION OF THE INVENTION

The present invention describes a process for the preparation of dried small particles of fenofibrate stabilized by phospholipid comprising the steps of (a) mixing in an aqueous carrier in the absence of an organic solvent at high shear and within a first temperature range at or above the melting point of the fenofibrate an admixture of fenofibrate and one or more than one surface active substance of which at least one is a phospholipid, and optionally one or more bulking agents, to form a heated suspension containing the drug, then (b) homogenizing said heated suspension in a first pressure range and within said first temperature range to form a heated homogenate containing the drug, optionally with the addition of one or more bulking agents at some time before, during or after the homogenization, then (c) spray drying the heated homogenate to form a dried composition of bulking agent and small particles containing the fenofibrate.

The present invention also provides a method of treating dyslipidemia and dyslipoproteinemia in a mammal which method comprises administering to said mammal a therapeutically effective oral dosage form comprising microparticles of a solid fibrate that are stabilized by a phospholipid surface active substance wherein said dosage form provides into the blood of said patient in a fasted state a therapeutically effective amount of said fibrate that is at least 90% of the AUC amount of said fibrate provided by said dosage form into the blood of said patient in a fed state. AUC refers to area under the curve.

In a preferred aspect, the present invention provides a method of treating dyslipidemia and dyslipoproteinemia in a human patient which method comprises administering to said patient a therapeutically effective oral dosage form comprising microparticles of a solid fenofibrate that are stabilized by a phospholipid surface active substance wherein said dosage form provides into the blood of said patient in a fasted state a therapeutically effective amount of fenofibrate active species that is at least 90% of the AUC amount of said fenofibrate active species provided by said dosage form into the blood of said patient in a fed state.

In another aspect the present invention also provides an orally administered pharmaceutical composition comprising microparticles of solid fibrate that are stabilized by a phospholipid surface active substance, wherein said microparticles are prepared in the presence of said phospholipid surface active substance, and wherein a therapeutically effective amount of said composition provides a quantity of fibrate active species to a fasted human patient in need of treatment by said fibrate that is greater than 90% of the quantity of said fibrate active species provided by said amount to said patient when fed a high fat meal.

In a preferred aspect the present invention also provides an orally administered pharmaceutical composition comprising microparticles of solid fenofibrate that are stabilized by a phospholipid surface active substance, wherein said microparticles are prepared in the presence of said phospholipid surface active substance, and wherein a therapeutically effective amount of said composition provides a quantity of fenofibrate active species to a fasted human patient in need of treatment by said fenofibrate that is greater than 90% of the quantity of said fenofibrate active species provided by said amount to said patient when fed a high fat meal.

In a preferred aspect, this invention provides a pharmaceutically effective composition comprising small particles of fenofibrate stabilized by a phospholipid stabilizing agent spray dried in the presence of a sugar and optionally also in the presence of a carbohydrate-derived alcohol that can be formulated as a capsule or tablet or powder or granular dosage form for oral administration to a patient in need of treatment by fenofibrate. The dosage form provides dosage levels of fenofibrate active species into the blood of a patient in a fasted or fed state wherein the amount of drug or active species that the patient receives in the fasted state differs by less than 25%, preferably by less than 20%, more preferably by less than 15%, even more preferably by less than 10%, and most preferably by less than 5% from the amount of drug or active species that the patient receives in the fed state.

This invention also describes an orally administered pharmaceutical composition comprising microparticles of solid fenofibrate that are stabilized by a phospholipid surface active substance, wherein said microparticles are prepared in the presence of said phospholipid surface active substance, and wherein a therapeutically effective amount of said composition provides a quantity of fenofibrate active species to a fasted human patient in need of treatment by fenofibrate that is greater than 80% of the quantity of fenofibrate active species provided by said amount to said patient when fed a high fat meal comprising at least 1000 calories 50% of which are from fat.

This invention also describes an orally administered pharmaceutical composition comprising microparticles of solid fenofibrate that are stabilized by a phospholipid surface active substance, wherein said microparticles are prepared in the presence of said phospholipid surface active substance and one or more excipients, and wherein a therapeutically effective amount of said composition provides a quantity of fenofibrate active species to a fasted human patient in need of treatment by fenofibrate that is greater than 80% of the quantity of fenofibrate active species provided by said amount to said patient when fed a high fat meal comprising at least 1000 calories 50% of which are from fat.

As used herein, a fasted patient is defined as a patient who does not eat any food, i.e. fasts for at least 10 hours before the administration of a dosage form of a drug such as fenofibrate and who does not eat any food and continues to fast for at least 4 hours after the administration of the dosage form The dosage form is administered with 180 ml of water during the fasting period, and water can be allowed ad libitum after 2 hours.

As used herein, a fed patient is defined as a patient who fasts for at least 10 hours overnight and then consumes an entire test meal within 30 minutes of first ingestion. The dosage form is administered with 180 ml of water within 5 minutes after completion of the meal. No food is then allowed for at least 4 hours post-dose. Water can be allowed ad libitum after 2 hours. A high fat test meal provides approximately 1000 calories to the patient of which approximately 50% of the caloric content is derived from fat content of the meal. A representative high fat high calorie test meal comprises 2 eggs fried in butter, 2 strips of bacon, 2 slices of toast with butter, 4 ounces of hash brown potatoes, and 8 ounces of whole milk to provide 150 protein calories, 250 carbohydrate calories, and 500 to 600 fat calories. High fat meals can be used in clinical bioequivalence and bioavailability studies of fenofibrate. High fat meals promote increased absorption and uptake of fenofibrate.

The absence or elimination of a food effect can be concluded when the 90% confidence intervals for the ratio of the geometric means based on log-transformed data in clinical studies of fed and fasted treatments fall within 80% to 125% for AUC (area under the concentration time curve) and 70% to 143% for $C_{max}$ (peak concentration). The presence of a food effect can be concluded when the 90% confidence intervals for the ratio of the geometric means based on log-transformed data in clinical studies of fed and fasted treatments fall outside 80% to 125% for AUC and outside 70% to 143% for $C_{max}$.

As used herein, "small particle" refers to a particle or a distribution of particles having a diameter or an average diameter, respectively, of from nanometers to micrometers. Small particles are microparticles, as used herein, and also refer to solid particles of irregular, non-spherical or spherical shapes.

As used herein, a homogenized molten microdroplet aqueous suspension of fenofibrate in the presence of and stabilized by a phospholipid surface active substance is also considered to be a homogenized molten microparticulate aqueous suspension of fenofibrate in the presence of and stabilized by a phospholipid surface active substance.

Water insoluble and poorly water soluble compounds are those having poor solubility in water at or below normal physiological temperatures, that is <5 mg/ml at physiological pH (6.5–7.4). Preferably their water solubility is <1 mg/ml, and more preferably <0.1 mg/ml.

A spray-dried solid form of fenofibrate microparticles is useful in formation of drug delivery compositions including capsules, tablets, powders, granules, and formulations with additional excipients and drugs.

Compositions of microfluidized fenofibrate stabilized with a phospholipid surface active agent prepared according to this invention and formulated according to this invention provide substantial reduction to elimination of the food effect that is observed with other formulations of fenofibrate.

Examples of some suitable surface active substances that are useful in the microfluidization process of this invention include: (a) natural surfactants such as casein, gelatin, tragacanth, waxes, enteric resins, paraffin, acacia, gelatin, cholesterol esters and triglycerides, (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylarnmonium bromide, chitosans and lauryldimethylbenzylammonium chloride, (e) colloidal clays such as bentonite and veegum. A detailed description of these surfactants may be found in Remington's Pharmaceutical Sciences, and Theory and Practice of Industrial Pharmacy, Lachman et al, 1986.

More specifically, examples of suitable surface active substances in addition to a phospholipid useful in this invention include one or combination of the following: polaxomers, such as Pluronic™ F68, F108 and F127, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylene-diamine available from BASF, Triton™ X-200, which is an alkyl aryl polyether sulfonate, available from Rohm and Haas. Tween 20, 40, 60 and 80, which are polyoxyethylene sorbitan fatty acid esters, available from ICI Speciality Chemicals, Carbowax™ 3550 and 934, which are polyethylene glycols available from Union Carbide, hydroxy propylmethylcellulose, dimyristoyl phosphatidylglycerol sodium salt, sodium dodecylsulfate, sodium deoxycholate, and cetyltrimethylammonium bromide. These are all pharmaceutically acceptable surface active substances.

Preferred surface active substances are phospholipid surface active substances. By phospholipid surface active substances or phospholipid surface active agents is meant a single phospholipid or a mixture of two or more phospholipids, for example a mixture of two or three or four or five or from six to about ten phospholipids. Suitable phospholipids include animal and plant phospholipids; egg phospholipids; soya bean phospholipids; corn phospholipids; wheat germ, flax, cotton, and sunflower seed phospholipids; milk fat phospholipids; glycerophospholipids; sphingophospholipids; phosphatides; phospholipids containing fatty acid esters including palmitate, stearate, oleate, linoleate, and arachidonate which esters can be mixtures and mixtures of isomers in the phospholipids; phospholipids composed of fatty acids containing one or more than one double bonds such as dioleoyl phosphatidylcholine and egg phosphatidylcholine that are not stable as powders but are hygroscopic and can absorb moisture and become gummy; phospholipids composed of saturated fatty acids that are stable as powders and are less amenable to absorption of moisture; phosphatidylserines; phosphatidylcholines; phosphatidylethanolamines; phosphatidylinositols; phosphatidylglycerols such as dimyristoyl phosphatidylglycerol, L-alpha-dimyristoyl phosphatidylglycerol also known as 1,2-dimyristoyl-sn-glycero-3-phospho(rac-1-glycerol) and also known as DMPG; phosphatidic acid; hydrogenated natural phospholipids; and commercially available phospholipids such as those available from Avanti Polar Lipids, Inc. of Alabaster, Alabama, USA. In the absence of an internal counterion in the phospholipid, a preferred counterion is a monovalent cation such as sodium ion. The phospholipid may be salted or desalted, hydrogenated, partially hydrogenated, or unsaturated, natural, synthetic, or semisynthetic.

Preferred phospholipids include Lipoid E80, Lipoid EPC, Lipoid SPC, DMPG, Phospholipon 100H a hydrogenated soybean phosphatidylcholine, Phospholipon 90H, Lipoid SPC-3, and mixtures thereof. A currently most preferred phospholipid is Lipoid E80.

The concentration of surface active substance added to the formulations prepared according to this invention can be present in the range of 0.1 to 50%, preferably 0.2 to 20%, and more preferably 0.5 to 10%. A currently preferred level of Lipoid E80 is from about 0.5% to 15%, more preferably from about 0.5% to about 10%, and most preferably from 0.5 to 5%.

In a preferred aspect, a process is provided for the preparation of small particles or microparticles containing fenofibrate and a phospholipid surface stabilizing substance which comprises the steps of:

(a) mixing at high shear an admixture of fenofibrate and a phospholipid substance in an aqueous carrier in the absence of an organic solvent and optionally in the presence of one or more than one surface active substances within a first temperature range at or above the melting point of the drug to form a heated suspension containing the drug, then (b) homogenizing said heated suspension in a first pressure range and within said first temperature range to form a heated homogenate containing the drug, then (c) spray drying the heated homogenate to form dried small particles containing the drug wherein one or more bulking agents is added at any stage of either of steps (a) or (b) and wherein at least one surface active agent is a phospholipid.

In a specific aspect, the present invention is directed to a composition and a process for the preparation of microparticles of fenofibrate, which small particles are used to prepare an orally administered pharmaceutical composition comprising said microparticles of solid fenofibrate that are stabilized by a phospholipid surface active substance, wherein said microparticles are prepared in the presence of said phospholipid surface active substance, and wherein a therapeutically effective amount of said composition provides a quantity of fenofibrate active species to a fasted human patient in need of treatment by fenofibrate that is greater than 80% of the quantity of fenofibrate active species provided by said amount to said patient when fed at least 1000 calories 50% of which are from fat.

The present invention also provides a dosage form of a pharmaceutical composition comprising a combination of a statin and microparticles of fenofibrate that are stabilized by a phospholipid surface active substance, wherein the microparticles of fenofibrate are prepared by a process comprising the steps of:

(a) mixing at high shear an admixture of fenofibrate and a phospholipid substance in an aqueous carrier in the absence of an organic solvent and optionally in the presence of one or more than one surface active substances within a first temperature range at or above the melting point of the drug to form a heated suspension containing the drug, then (b) homogenizing said heated suspension in a first pressure range and within said first temperature range to form a heated homogenate containing the drug, then (c) spray drying the heated homogenate to form dried small particles containing the drug wherein one or more bulking agents is added at any stage of either of steps (a) or (b).

In another aspect, this invention also provides a method of treatment of dyslipidemia and dyslipoproteinemia and related diseases in a patient comprising the administration to said patient of a dosage form of the aforementioned pharmaceutical compositions comprising a combination of a statin and microparticles of fenofibrate that are spray dried from a molten heated homogenate.

This invention also describes an orally administered combination pharmaceutical composition comprising spray dried microparticles of solid fenofibrate that are stabilized by a phospholipid surface active substance and a statin, wherein said microparticles are prepared in the presence of said phospholipid surface active substance and one or more excipients and spray dried from a molten heated homogenate, and wherein a therapeutically effective amount of said composition provides a quantity of fenofibrate to a fasted human patient in need of treatment by fenofibrate that is greater than 80% of the quantity of fenofibrate provided by said amount to said patient when fed a high fat meal comprising at least 1000 calories 50% of which are from fat.

The combination of statin and spray dried phospholipid-stabilized microparticles that exhibit a substantial reduction in food effect as described in this invention can be employed in a number of dosage forms including tablets, capsules, and powders, which powders can be dispersed in a beverage such as a citrus beverage (e.g., orange juice and the like) or a food beverage such as a vegetable juice, or a flavored beverage sometimes used by a patient on a restricted calorie diet or a restricted fat diet such as Slim-Fast™ and similar beverages. Particularly useful also are the dosage forms disclosed in WO 00/30616, the contents of which is hereby incorporated by reference.

In one embodiment of the combination of a statin and spray dried microparticles of fenofibrate stabilized by a phospholipid surface active substance of this invention, sometimes hereinafter referred to as Fenostatin and disclosed herein, a desired amount of a statin can be added at any step of the preferred process, but preferably can be added to the heated homogenate containing fenofibrate just prior to spray drying. Alternatively, the statin can be added to the spray dried powder. This is particularly preferred when the statin is thermally or hydrolytically labile.

A desired amount of statin to be present in a dosage form of this invention can be determined in one aspect based on the clinically practiced daily dose amount of the statin. Thus for example, for simvastatin the amount to be added to the cooled homogenate will be between 5% to 30% relative to the amount of fenofibrate, and preferably between 7% to 15%. A statin can be added to the admixture or heated homogenate of fenofibrate as powder or as a solution depending on its solubility in an aqueous carrier used such as 10 mM phosphate buffer at pH 8. In the case of lovastatin, simvastatin, itavastatin and certain others, the lactone ring may open to the corresponding hydroxyacid form or a salt thereof under certain aqueous buffer conditions.

In the dosage forms of the current invention, the statin can be water soluble, water insoluble, or poorly water soluble.

In the dosage forms of the current invention, particularly when the statin is water insoluble or poorly water soluble, the statin can be in the form of a microparticle or can be a constituent of a microparticle, preferably in the form of a microparticle that is stabilized by one or more surface active substance or is a constituent of a microparticle that is stabilized by one or more surface active substance. In this aspect, a preferred surface active substance comprises a phospholipid.

In the dosage forms of the current invention, the statin is selected from the group consisting of lovastatin, pravastatin, simvastatin, atorvastatin, rosuvastatin, fluvastatin, itavastatin, and cerivastatin. In preferred embodiments of the dosage forms of this invention, the statin can be lovastatin where the lovastatin is present in the range of 2 mg to 50 mg; the statin can be pravastatin present in the range of 2 mg to 50 mg; the statin can be simvastatin where the simvastatin is present in the range of 2 mg to 100 mg; the statin can be atorvastatin where the atorvastatin is present in the range of 2 mg to 100 mg; the statin can be rosuvastatin where the rosuvastatin is present in the range of 2 mg to 100 mg; the statin can be fluvastatin where the fluvastatin is present in the range of 2 mg to 50 mg; the statin is itavastatin where the itavastatin is present in the range of 0.2 mg to 100 mg; the statin is cerivastatin where the cerivastatin is present in the range of 0.05 mg to 2 mg.

In the compositions of this invention, the statin can be water-soluble or water insoluble or poorly water-soluble. In one aspect of this invention, the dosage forms of this invention can contain water insoluble or poorly water-soluble statins in the form of microparticles such as a phospholipid stabilized microparticles of a solid statin core, or as a constituent of a microparticle such as may occur if the statin is present in a microparticle core comprising fenofibrate. Preferred statins are lovastatin, pravastatin, simvastatin, atorvastatin, rosuvastatin, fluvastatin, itavastatin, and cerivastatin.

The amount of a statin in a dosage form of this invention will depend on which statin is used for the combination formulation. For example, for a combination comprising microparticles of spray dried fenofibrate prepared according to this invention and simvastatin, the amount of simvastatin per capsule or tablet can range from about 1 mg to about 20 mg and in some cases up to 100 mg, although preferably it will be from 5 mg to about 10 mg.

For a combination comprising fenofibrate prepared according to this invention and lovastatin, the amount of lovastatin in a dosage form of this invention is in the range of 2 mg to 50 mg although preferably it will be from 10 to 40 mg.

For a combination comprising fenofibrate prepared according to this invention and pravastatin, the amount of pravastatin in a dosage form of this invention is in the range of 2 mg to 50 mg although preferably it will be from 10 to 40 mg.

For a combination comprising fenofibrate prepared according to this invention and atorvastatin, the amount of atorvastatin in a dosage form of this invention is in the range of 2 mg to 100 mg although preferably it will be from 5 to 80 mg, and more preferably from 5 to 20 mg.

For a combination comprising fenofibrate prepared according to this invention and rosuvastatin, the amount of rosuvastatin in a dosage form of this invention is in the range of 2 mg to about 80 mg although preferably it will be from 5 to 20 mg.

For a combination comprising fenofibrate prepared according to this invention and fluvastatin, the amount of fluvastatin in a dosage form of this invention is in the range of 2 mg to 50 mg although preferably it will be from 20 to 40 mg.

For a combination comprising fenofibrate prepared according to this invention and itavastatin, the amount of itavastatin in a dosage form of this invention is in the range of 0.1 to about 20 mg although preferably it will be from 2 to 10 mg.

For a combination comprising fenofibrate prepared according to this invention and cerivastatin, the amount of cerivastatin in a dosage form of this invention is in the range of 0.02 mg to 1.2 mg although preferably it will be from 0.2 to 0.8 mg.

An admixture of fenofibrate and a phospholipid surface active substance can be prepared by adding a phospholipid substance and fenofibrate to an aqueous carrier and then mixing at high shear for up to 30 minutes at a shear rate of up to 10,000 rpm. Preferably fenofibrate used to form the admixture is in the form of a powder or small crystals or small pieces that are less than about 5 mm in diameter to facilitate mixing. Larger sized crystals or masses of drug can be milled to about 5 mm or smaller before forming the admixture used in this invention to facilitate mixing.

Suitable aqueous carriers include water, sterile water, water for injection, and buffered water such as phosphate buffered water. The pH of the buffer can be in the range of from 4 to 10, preferably from 7 to 9, and most preferably from 7.5 to 8.5. A preferred aqueous carrier is 0.01 to 10 mM sodium phosphate buffer. The pH of the carrier is preferably established at room temperature before mixing with the phospholipid substance and the fenofibrate and before heating to a first temperature. The pH may be adjusted by addition of an acid or base such as HCl or NaOH to a solution of a phosphate salt. Preferably the aqueous carrier contains no dissolved oxygen. A currently most preferred aqueous carrier is 10 mM phosphate buffer.

In one aspect, the aqueous carrier can initially be at a temperature between about 1° C. to about 100° C., preferably between 20° C. and 90° C., and more preferably between 20° C. and 50° C. This is particularly useful for fenofibrate. The aqueous carrier can be heated to the desired first temperature range before or after the addition of the admixture.

After the fenofibrate and a phospholipid substance are added to the aqueous carrier, the admixture can then be heated if not already so, preferably in the absence of oxygen such as under a nitrogen or argon atmosphere, until the temperature rises to a first temperature range that is at or above the melting point of the drug. In the case of fenofibrate the admixture in the aqueous carrier can be heated to between 79° C. (the reported lowest melting point of fenofibrate) and 99° C., preferably between 79° C. and 95° C., and most preferably between 80° C. and 90° C. It is preferred that the temperature is at or up to about 20° C. above the melting point of the drug. Thus, the preferred first temperature range is in general from the melting point of the drug to about 20° C. above the melting point of the drug. The aqueous carrier can be heated to the first temperature range before or after the addition of the drug and the surface active substance. The admixture is maintained at the first temperature range while high shear mixing is applied. The admixture when thus prepared comprises a crude emulsion of melted drug and surface active substance in the heated aqueous carrier.

During the heating of the admixture, high shear mixing is applied. Suitable shear is derived for example from propeller-containing mixers, homogenizers, blenders, sonicators or other devices capable of producing a heated suspension. Suitable shear rates can range between 500 to 10,000 rpm, preferably 2,000 to 5,000 rpm. High shear mixing can be continued for up to 30 minutes or even longer if needed to form a heated suspension containing the drug. High shear mixing of the admixture when the temperature is below the melting point of the drug provides a suspension of the admixture in the aqueous carrier, and such suspension is useful as an antecedent to the heated suspension that is produced when the temperature is increased to or above the melting point of the drug. Continued application of high shear mixing or application of more vigorous or ultra-high shear mixing when the temperature is above the melting point of the drug can produce a heated homogenate of the admixture in the aqueous carrier. When the temperature is above the melting point of the drug, the heated suspension is a suspension of melted drug and surface active substance in the aqueous carrier. In one aspect, the heated suspension is an emulsion of melted drug and surface active substance in the aqueous carrier. High shear mixing and ultra-high shear mixing can be produced by the input of mechanical energy for example using a mechanical mixer or stirrer or mill configured with a mixing blade or propeller that can induce efficient mixing and particle size reduction through high shear turbulence, turbulent eddies, transfer of high fluid kinetic energy, high energy dissipation, pressure induced cavitation, and similar known mechanisms of homogenization.

In one aspect, devices useful in the preparation of a heated suspension of this invention can be employed in the preparation of the heated homogenate of this invention if sufficient energy is transferred to the particles of the heated suspension to produce a heated homogenate. In this case, heating of the admixture to form a heated suspension and then homogenization of the heated suspension to form a heated homogenate can be done as a continuous step combining step (a) and step (b) into a single step wherein a heated suspension is formed and then converted into a heated homogenate with out substantial change in apparatus or without substantial increase in energy applied to the heated admixture formulation.

Preferably one or more bulking agents is added during step (a) and/or during step (b).

As used herein, homogenization refers to the creation of a homogenate or uniform distribution of small particles containing drug in an aqueous carrier as a result of an energetic process being applied to an antecedent composition such as a mixture, admixture, blend, emulsion, suspension, dispersion or other composition of solids or solid particles or liquids or liquid particles or droplets comprising drug and one or more than one surface active substance in an aqueous carrier wherein the homogenate and the small particles produced are at least transiently stable toward phase separation into larger particles or droplets or non-uniform solid or liquid domains. Homogenization, particularly with respect to the formation of a heated suspension and a heated homogenate, can be achieved by input of mechanical energy such as by high shear mixing, ultra high shear mixing, high speed blending, microfluidization, and milling such as by dispersion milling, ball milling, attritor milling, vibrator milling, and media milling, or by application of sonic energy in the form of sonication. Preferably in the case of a mill being used in this process wherein the mill contains media or grinding media, such media is removed in a filtration or other suitable separation process to provide homogenized compositions of this invention. Homogenization is preferably achieved by passing an antecedent composition under high pressure, for example under more than 1000 psi, through a tiny orifice which can result in a decrease in the average diameter and an increase in the number and surface area of particles or droplets in the antecedent composition and produce small particles. A preferred homogenization method comprises passing an antecedent composition under high pressure through a tiny orifice and includes microfluidization.

The fenofibrate can be added to the aqueous carrier as a solid. Preferably the fenofibrate can be added in the form of particles ranging in size up to about 10 mm such as milled or micronized particles or powders. Milled particles can be obtained for example by air jet milling of bulk powdered or crystalline fenofibrate. The drug can also be added to the aqueous carrier as a molten material, i.e., heated at or above its melting point, preferably at the melting point of the drug to about 20° C. above the melting point of the drug but at a temperature less than its decomposition point. For fenofibrate the preferred temperature can be from about 80° C., the melting point of the drug, to about 100° C. although temperatures up to the decomposition point of the drug are also suitable.

The concentration of the surface active substance in the aqueous carrier can vary between 0.1% w/w and 90% w/w, preferably between 0.1% w/w and 50% w/w, and more preferably between 0.2% and 20%, and most preferably between 0.5% to 10% w/w. The concentration of the fenofibrate in the aqueous carrier can vary between 0.1% w/w and 90% w/w, preferably between 0.5% w/w and 50% w/w, and more preferably between 1% and 20% w/w. For example, in one aspect a currently preferred composition comprises 3% to 10% of a phospholipid substance as a surface active substance and 10% of fenofibrate in 10 mM phosphate buffer at pH 8 as an aqueous carrier. Another currently preferred composition comprises 0.5% of a phospholipid substance as a surface active substance and 10% of the poorly water soluble drug fenofibrate in 10 mM phosphate buffer at pH 8 as an aqueous carrier. Another currently preferred composition comprises 1.5% of a phospholipid substance as a surface active substance and 10% of the poorly water soluble drug fenofibrate in 10 mM phosphate buffer at pH 8 as an aqueous carrier.

The surface active substance can be added to the aqueous carrier at any temperature below its decomposition point. When used as a mixture of surface active substances, the individual components can be added separately to the aqueous carrier or combined as mixtures before addition. The surface active substance can be added together with the fenofibrate or separately to the aqueous carrier.

The admixture of the fenofibrate and a surface active substance such as a phospholipid substance in an aqueous carrier is heated to a first temperature range during the application of a high shear mixing to produce a heated suspension containing the drug.

The heated suspension containing the drug is then homogenized at the first temperature range to form a heated homogenate. The first temperature range is maintained during this homogenization to ensure that the drug is maintained in a molten state. For fenofibrate, the first temperature range is preferably from 79° C. to 100° C. and more preferably from 80° C. to 100° C. provided that fenofibrate remains molten.

Homogenization of the heated suspension containing the drug can be carried out in equipment suitable for that process. Useful equipment includes commercially available high pressure homogenization equipment such as APV Gaulin M15, Avestin Emulsiflex C5 or C50, and MFIC Microfluidizer M110EH and other commercially available microfluidizers and commercially available microfluidizers modified to accommodate heat exchangers and temperature monitoring devices and piping and valves to carry heated suspensions or emulsions. The microfluidizers can be heated to the first temperature range, for example by use of electrical resistance, heated air bath, or heated fluid bath such as a water or silicone oil bath heated to the first temperature range that is at or above the melting point of the drug.

Homogenization of the heated suspension containing the drug is done at a first pressure range in the homogenization chamber of a heated homogenization apparatus while the drug is maintained in its molten state. The first pressure range can be from 2,000 psi to 30,000 psi, preferably about 5,000 psi to 20,000 psi, and more preferably from about 3,000 psi to about 10,000 psi.

The heated suspension containing the drug can be processed into the homogenization chamber of the homogenization apparatus by gravity feed from a heated and optionally stirred reservoir or by aid of a pump, for example a peristaltic pump, from a reservoir heated to the first temperature range through the heated homogenization chamber of the heated homogenizer and thence into a heated receiving vessel heated to the first temperature range in such a manner as to ensure the entire fluid volume of the heated suspension is subjected to discrete homogenization resulting in a homogeneous suspension of heated submicron or micron molten particles. In one aspect of this invention, between each homogenization pass the processed heated suspension is returned batch-wise from the heated receiving vessel back into the heated reservoir such as by means of a pump or by pouring, and the heated homogenization step is repeated. In another aspect, the processed heated suspension is fed directly back into the heated reservoir in a continuous process. If the initial volume of the heated suspension before homogenization is defined as a volume pass, then the number of volume passes made through the homogenizer in this manner can range from one to about 20, preferably from one to ten, more preferably from 2 to 8, and most preferably from 3 to 7 to produce a heated homogenate that is initially at the first temperature range at or above the melting point of the drug. A preferred drug in this process is fenofibrate which has a preferred first temperature range of from 80° C. to about 95° C.

While it is not known with certainty, it is appreciated that forcing a drug and a surface active substance such as a phospholipid under conditions of elevated pressure and temperature through a microfluidizing chamber can cause transient gradients in temperature, the microfluidization process being exothermic and causing a rise in the temperature of the processed suspension of particles or emulsions during particle size reduction. While the transient rise in temperature is usually controlled by a temperature regulating device such as a heat exchanger, it is possible that transient concentration gradients of poorly water soluble drug and stabilizer are established or continue to exist in the rapidly moving non-equilibrium state of the microfluidizer. Water insoluble or poorly soluble components of the formulation (e g., fenofibrate and phospholipid) may be forced into solution temporarily, perhaps at a molecular level thereby creating a supersaturated or molecularly distorted environment which if left undisturbed will subsequently achieve equilibrium again. It is postulated that transient concentration gradients may be established in the microfluidization process wherein molecules of drug and stabilizer are forced into an aqueous environment to give a transiently stable but novel composition and non-equilibrium condition.

Contrary to the expectations of U.S. Pat. No. 5,700,471, the heated homogenate can be spray dried to provide a dried powder comprising stabilized microparticles of fenofibrate and a bulking agent. During the spray drying process, atomized droplets of heated homogenate experience a temperature gradient that cools the molten fenofibrate and other components of the heated homogenate. The particles solidify in the presence of the bulking agent without the formation of large crystals and without the formation of agglomerates that cannot be redispersed on rehydration.

To approximate the cooling experienced by the novel composition of the heated homogenate in the spray drying process, the heated homogenate can be cooled in bulk to a transiently stable or metastable cooled homogenate. By metastable we mean that upon agitation or long-term standing the transiently stable particles of the cooled homogenate will convert to larger particles of crystallized or precipitated drug and can demonstrate phase separation of components of the homogenate from the aqueous carrier. For example, under these conditions fenofibrate forms a transiently stable or metastable cooled homogenate that on standing or application of manual agitation such as shaking or stirring produces larger crystals. The lifetime of the transiently stable particles of the cooled homogenate can be moderately extended by control of cooling conditions.

In one aspect particle size of the heated homogenate can be measured using a laser light diffraction based instrument such as a Malvern Mastersizer Microplus and shown to be less than one micrometer.

If an attempt is made to collect the heated homogenate in a receiving vessel that is not preheated to the first temperature, fenofibrate immediately precipitates from the heated homogenate as solid crystals. This is very likely related to agitation of the transiently stable dispersion.

In the case of fenofibrate, microscopic examination of a heated homogenate shows it to be comprised of small and non-crystalline particles in suspension, but there is a tendency for fenofibrate to crystallize out on the microscope slide. This rapid crystallization is also seen if the heated homogenate is collected in a receiver at ambient temperature.

A transiently stable or metastable cooled homogenate can be obtained from a heated homogenate derived from an admixture of drug and a surface active substance such as a phospholipid substance in an aqueous carrier by rapidly cooling the heated homogenate under non-agitating conditions from a first temperature range at or above the melting temperature of the drug to a second temperature range below the melting point of the drug, preferably to the range of 1° C. to about 20° C.

The heated homogenate can be held at the first temperature range that is above the melting point of the drug. Agitation during the holding period above the melting point of the drug does not effect crystallization of the drug. The heated homogenate can be spray dried immediately or can be held at the first temperature range for up to several hours and then spray dried. The unexpected stability of the heated homogenate towards particle size increase permits the heated homogenate to be spray dried without the formation of large crystals, precipitates, or irreversible agglomerates.

The stability of the heated homogenate of this invention containing fenofibrate is demonstrated by the formation of a transiently stable cooled homogenate. In the case of fenofibrate a transiently stable or metastable cooled homogenate can be obtained from a heated homogenate derived from an admixture of fenofibrate and a phospholipid substance in an aqueous carrier by rapidly cooling the heated homogenate under non-agitating conditions from a first temperature range at or above the melting temperature of fenofibrate to a second temperature range below the melting point of fenofibrate, preferably to the range of 1° C. to about 20° C. Under non-stirred conditions the cooled homogenate retains small non-crystalline particles very similar to those detected initially in the heated homogenate. Optionally, the heated homogenate can be held at the first temperature range, for example at 80° C. to 90° C., for a holding time before the onset of cooling to the second temperature range. Agitation during the holding period does not effect crystallization of the fenofibrate.

A number of cooling methods can be applied to the heated homogenate containing a poorly water soluble drug to cool it from the first temperature range at or above the melting point of the drug to a temperature below the melting point of the drug to form a cooled homogenate. Examples of several methods are listed and illustrated with respect to fenofibrate as follows.

Method 1: slow cooling in ambient air optionally in a closed vessel that excludes oxygen and air by allowing the heated homogenate to stand unagitated and to cool from above the melting point of the drug to ambient room temperature;

Method 2: slow unagitated cooling from above the melting point of the drug which for fenofibrate is about 85° C. in a water bath at ambient temperature which is approximately 15° C. to 20° C.;

Method 3: slow stepwise cooling at 1 degree Centigrade per minute in a stirred oil bath from above the melting point of the drug to ambient temperature;

Method 4: slow stepwise cooling from above the melting point of the drug to about 20° C. below the melting point of the drug which for fenofibrate is from about 85° C. down to 65° C., followed by cooling to 4° C. in an isothermally cooled 4° C. water bath;

Method 5: fast cooling in an isothermally cooled 4° C. water bath;

Method 6: slow stepwise cooling from above the melting point of the drug to about 40° C. below the melting point of the drug which for fenofibrate is from about 85° C. to about 40° C. at the rate of 1 Centigrade degree per minute.

The effect of stirring during the cooling phase was examined for fenofibrate as an example. In some studies, samples were left unagitated while others were stirred magnetically at 250 rpm using Teflon-coated magnetic stirring bars during cooling methods. Additionally, in some experiments, heated homogenate was diluted ten fold with additional aqueous carrier that had been heated to the first temperature, the diluted heated homogenate was then swirled to evenly distribute the added aqueous carrier, and then the diluted heated homogenate was cooled.

Particle size determinations were carried out using a Malvern Microplus Mastersizer. Samples were examined at two to three hours after the initiation of cooling. Results are reported as volume weighted averages or D(4,3). Samples were also examined microscopically under bright polarized light using both in-phase and out-of-phase modes. In-phase light allowed determination of the primary particle size and the detection of aggregates. Out-of-phase examination gave an indication of the amount of crystals formed in the composition. Morphologically small crystalline particles of fenofibrate were easily distinguished from large fenofibrate crystals.

When 3% Lipoid E80 (also sometimes referred to as E80 herein below) was used as a phospholipid substance in a single pass homogenization preparation of a heated homogenate containing 10% fenofibrate, little difference was observed in the particle characteristics when cooled by either method 1 or 2 (average particle size at 3 hours was 2.42 and 2.96 micrometers, respectively). The particles were initially non-crystalline, spherical and submicron but crystals appeared within 3 hours. In contrast, when 3% Lipoid E80 was used as a phospholipid substance in a two pass homogenization preparation of a heated homogenate containing 10% fenofibrate, a smaller particle size was unexpectedly observed when a sample was cooled by method 1 versus when a sample was cooled by method 2 (0.56 and 1.64 micrometers, respectively after 3 hours of cooling). This difference was different from that seen in heated homogenates prepared with saturated lipids such as phospholipon 100H (also sometimes referred to as 100H herein below) and phospholipon 90H (also sometimes referred to as 90H herein below) when processed for two passes. In these formulations, the particle size at 2 to 3 hours after initiation of cooling was significantly higher than that seen using Lipoid E80. For heated homogenates prepared using 3% phospholipon 100H in two passes and cooled for 3 hours according to methods 1 and 2, the average particle sizes were 14.72 and 10.31 micrometers, respectively. For heated homogenates prepared using 3% phospholipon 90H in two passes and cooled for 2 hours according to methods 1 and 2, the average particle sizes were 6.07 and 5.23 micrometers, respectively. Microscopically the cooled homogenates containing phospholipon 100H and phospholipon 90H consisted of particle aggregates with crystals appearing over time. Aggregates were not typically seen in Lipoid E80 formulations but crystal growth occurred over time.

Increasing the cooling rate in the absence of agitation produced cooled homogenates that maintained small particles containing fenofibrate to a greater degree than those produced by slow cooling methods. This was especially true when Lipoid E80 was used as the phospholipid substance. For example, when a sample of heated homogenate prepared from 3% Lipoid E80 as the surface active substance and 10% fenofibrate in two homogenization passes was cooled by method 5 (fast cooling) and compared to a cooled sample of heated homogenate of the same composition cooled according to methods 1 or 2 (slow cooling), the particle size at 3 hours for fast cooling was 0.63 micrometers versus 0.76 micrometers for slow cooling.

For non-stirred samples, minimal particle size increases can be observed in all cooling methods while under stirred conditions substantial crystallization or precipitation or agglomeration of poorly water soluble drug can be observed. For example, for non-stirred samples containing fenofibrate, minimal particle size increases were observed in all cooling methods. In contrast, under stirred conditions substantial crystallization of fenofibrate was observed for all cooling methods. For samples cooled in a slow step process, crystal growth occurred at temperatures lower than about 20° C. below the melting point of the drug, i.e., for fenofibrate below about 60° C.

Diluting the heated homogenate ten fold with additional heated aqueous carrier was found unexpectedly to have a beneficial effect on the size of particles when cooled. Results for fenofibrate as an example are displayed in Table 2. Attention is drawn to the bottom two rows of Table 2 which show that the particle size of diluted suspension of fenofibrate is smaller than that of undiluted suspension.

TABLE 2

Effect of dilution with aqueous carrier on cooled particle sizes in micrometers of heated homogenate containing 10% fenofibrate and 3% phospholipid

| Phospholipid (one pass) | E80 | E80 | 100H | 100H | 90H | 90H |
|---|---|---|---|---|---|---|
| Cooling method (time of cooling) | 1 (3h) | 2 (3h) | 1 (3h) | 2 (3h) | 1 (2h) | 2 (2h) |
| Undiluted average particle size | 2.42 | 2.96 | 11.46 | 9.71 | 4.83 | 4.12 |
| Diluted average particle size | 1.84 | 1.69 | 3.29 | 3.77 | 2.17 | 2.73 |

Particle size of less than 1 micrometer can usually be achieved by subjecting the heated homogenate containing melted drug to multiple homogenization passes. The effect of multiple homogenization is to produce smaller particles, but the size reducing effect is non-linear and shows decreasing rates of return, i.e., the average particle size decreases non-linearly with an increasing number of passes.

In the case of fenofibrate, it was also found that increasing the number of heated homogenization passes from one to two followed by cooling produced a cooled homogenate with smaller particle size with Lipoid E80 but not with Phospholipon 100H or Phospholipon 90H. For example, at 3 hours after cooling, a cooled homogenate sample containing fenofibrate prepared according to method 1 had a particle size of 0.56 micrometers when the antecedent heated homogenate had been subjected to two passes of homogenization compared to a particle size of 2.42 micrometers when the antecedent heated homogenate had been subjected to one homogenization pass. When a heated homogenate had been subjected to 10 homogenization passes, the cooled homogenate had a particle size of 0.29 micrometers. It was generally found that cooled homogenate having particle size of about 0.3 micrometers could be achieved from heated homogenate that had been subjected to at least 5 homogenization passes. Additional homogenization produced smaller particles, but at decreasing rates per volume pass. For examples, particles as small as 0.05 micrometers can be achieved under homogenization conditions. Results for one and two homogenization volume passes as a function of phospholipid are displayed in Table 3.

TABLE 3

Difference between one and two heated homogenization passes on cooled particle sizes in micrometers of heated homogenates containing 10% fenofibrate and 3% phospholipid

| Phospholipid (no. of passes) | E80 | E80 | 100H | 100H | 90H | 90H |
|---|---|---|---|---|---|---|
| Cooling method (time of cooling) | 1 (3h) | 2 (3h) | 1 (3h) | 2 (3h) | 1 (2h) | 2 (2h) |
| One pass average particle size | 2.42 | 2.96 | 11.46 | 9.71 | 4.83 | 4.12 |
| Two pass average particle size | 0.56 | 1.64 | 14.72 | 10.31 | 6.07 | 5.23 |

We have also found that the pass dependent particle size of the cooled homogenate can be a function of the ratio of the concentration of surface active substance to drug. For example, a heated homogenate prepared using 3% Lipoid E80 as the surface active substance and 10% fenofibrate as the drug and subjected to 10 homogenization passes produced a cooled homogenate by method 6 that had a particle size of 0.35 micrometers while a heated homogenate prepared using 10% Lipoid E80 as the surface active substance and 10% fenofibrate as the drug and subjected to 10 homogenization passes produced a cooled homogenate by method 6 that had a particle size of 1.3 micrometers.

Furthermore, when a heated homogenate was prepared using 3% Phospholipon 100H as the surface active substance and 10% fenofibrate as the drug, subjected to 10 homogenization passes and cooled, a cooled homogenate was produced by method 5 that had a particle size of 1.45 micrometers. In comparison, when a heated homogenate was prepared using 3% Lipoid E80 as the surface active substance and 10% fenofibrate as the drug, subjected to 10 homogenization passes and cooled, a cooled homogenate was produced that had a particle size of 1.3 micrometers.

Fast cooling of heated homogenates in a 4° C. bath under non-stirred conditions produces cooled homogenates with minimum change in morphology and particle size from that observed in the heated homogenates prior to cooling. For example, we have discovered that fast cooling of heated homogenates containing a phospholipid as the surface active substance and fenofibrate as the drug in a 4° C. bath under non-stirred conditions produced non-crystalline cooled homogenates with minimum change in morphology and particle size from that observed in the heated homogenates prior to cooling. When samples of heated homogenate were held at 80° C. for up to one hour and then cooled to form cooled homogenates that were held for 30 minutes at 5° C., no differences in particle size could be detected as a function of the time the heated homogenate was held at 80° C. before cooling. For optimum processing speed, freshly prepared samples of heated homogenate can be cooled from the first temperature range to a second temperature range immediately after an adequate number of homogenization passes such as five passes of heated homogenization to provide cooled homogenates. However, cooled homogenates thus prepared appear to be transiently stable or metastable toward formation of crystals of drug that can grow larger and precipitate from the suspension of the cooled homogenate if allowed to stand. The formation of larger particles and crystals is enhanced if the cooled homogenate is disturbed such as by stirring or shaking.

Preferably, the average particle size of the microparticles of fenofibrate stabilized with phospholipid is less than 10 microns, more preferably less than 5 microns, even more preferably less than 4 microns, yet even more preferably less than 3 microns, yet even more preferably less than 2 microns, and most preferably less than 1 micron. Microparticles that are less than about 0.5 microns are especially preferred.

The homogenization of molten fenofibrate by the process of this invention can produce particles that have an average particle size of about 0.5 microns or less, and as small as 0.1 microns. The size of these particles can be maintained by spray drying the molten heated homogenate if the concentration of the particles is maintained below about 10% by weight of the heated homogenate or if the heated homogenate is diluted with hot water and spray dried at a low concentration, between 0.5% and about 10%.

In another aspect of the process, the amount of bulking agent present in the heated homogenate can be increased by up to as much as 50% or more, and the heated homogenate can be spray dried to provide small particles.

In another aspect of this invention, bulking agents or bulking agent excipients can be added as solids or in solutions of aqueous carrier to the admixture of drug and a surface active substance in an aqueous carrier in the process of this invention.

A bulking agent is herein defined as compound useful in assisting redispersion of dried small particles back into a suspension such as an aqueous suspension. Suitable bulking agents include hydroxyl-containing, hydrophilic, relatively low molecular weight (less than 50,000) compounds such as monosaccharides, disaccharides, trisaccharides, sucrose, raffinose, lactose, mannitol, sorbitol, trehalose, glycerol, dextrose, maltodextrose, fructose, sugars, pentoses, hexoses, xylitol, and mixtures thereof.

Optionally, bulking agents can include one or more amino acids, preferably naturally occurring or essential amino acids, proteins, peptides, vitamins such as vitamin A, vitamin C (ascorbic acid), citric acid, cellulose and modified cellulose acceptable for pharmaceutical or food use such as carboxymethylcellulose and salts thereof, albumin, aspartame, povidone, crospovidone, croscarmellose sodium (Ac-Di-Sol) and related salts, additional phospholipid such as egg lecithin, magnesium salts such as magnesium stearate, magnesium carbonate, magnesium aluminum silicate, magnesium trisilicate, maltodextrin, polyethylene glycol, pluronic surfactants, polyethylene glycol esters acceptable for pharmaceutical use, polyethylene glycol ethers acceptable for pharmaceutical use, polymethacrylates acceptable for pharmaceutical use, polyvinyl alcohol acceptable for pharmaceutical use, polyvinyl acetate and partially hydrolyzed polyvinyl acetate acceptable for pharmaceutical use, saccharin, sodium saccharin, potassium sorbate, silicon dioxide, sodium lauryl sulfate, sorbitol, starch and modified starch, pharmaceutically acceptable organic acids such as stearic acid, palmitic acid, tartaric acid, sorbic acid, fumaric acid, alginic acid, lactic acid, edetic acid, and pharmaceutically acceptable salts thereof, pharmaceutically acceptable flavorings, pharmaceutically acceptable coloring agents, and other pharmaceutically acceptable excipients such as pharmaceutically acceptable diglycerides and triglycerides, pharmaceutically acceptable fatty acids such as oleic acid, stearic acid, palmitic acid, and myristic acid, fatty acid sorbitan esters, Tween surfactants, PEG-castor oil surfactants, omega-3-fatty acids and their salts, and mixtures thereof. These bulking agents can be added in amounts from about 0.5% to about 60% by weight to a dried powder and then formed into tablets or capsules or powders or granular dosage forms.

In another aspect, bulking agents such as those listed herein can be added as excipients to the stabilized particles of this invention either in suspension or as spray dried powders and then blended and formed into dosage forms such tablets, capsules, powders, and suspension of particles.

Bulking agents are useful as protectants or as additives in a spray drying process preventing or substantially reducing particle fusion, combination, suspension degradation and agglomeration during drying, and assisting in the resuspension of particles from a dried state.

Bulking agents can be added in amounts from 0.1% to about 50% w/w or more depending on the intended use. Additional amounts of bulking agents can be added to the phospholipid-stabilized microparticles after they have been prepared as a suspension, for example prior to the spray drying step, or after they have been dried or substantially dried. Mixing of bulking agents to dried or substantially dried microparticles can be done by mixing the ingredients or by adding one or more bulking agents to the microparticles or vice versa and subsequently blending the ingredients.

Depending on the intended use and ultimate formulation and dosage form, bulking agents such as monosaccharides, disaccharides, trisaccharides, sucrose, raffinose, lactose, mannitol, sorbitol, trehalose, glycerol, dextrose, maltodextrose, fructose, sugars, pentoses, hexoses, xylitol, and mixtures thereof can be added in amounts varying from about 0.1% up to their solubility limits in this aspect. A preferred range of these ingredients is such to provide from about 1% to about 90% of a tablet or capsule dosage form. A preferred range for the active ingredient, a fibrate such as fenofibrate in a tablet form 10% to about 90% by weight of the tablet, with a more preferred range being from about 15% to about 60%.

In yet another aspect of this invention, the phospholipid-stabilized microparticles can be sprayed onto the surface of a bulking agent, for example if the bulking agent is in the form of a particle or bead, a suspension of phospholipid-stabilized microparticles optionally containing dissolved or suspended bulking agent can be spray coated onto the surface of the bulking agent particle or bead to create a layer and optionally a multilayer derived from repetitive spray coating.

Preferred bulking agents include mannitol, trehalose, sucrose, sorbitol, and mixtures thereof. Preferred levels of these bulking agents in the admixture range from about 1% to about 30% w/w, and more preferably from about 2% to about 25% w/w.

The phospholipid-stabilized microparticles that exhibit a substantial reduction in food effect as described in this invention can be employed in a number of dosage forms. Particularly useful are the dosage forms disclosed in WO 00/30616 the contents of which is hereby incorporated by reference.

When trehalose was added to an admixture of fenofibrate and a phospholipid substance in an aqueous carrier, on stirring crystals were detected indicating that trehalose did not stabilise these metastable formulations with respect to crystal formation and precipitation. PVP 17 and glycerol were added to heated homogenates, and in both cases crystal growth was observed microscopically under stirred conditions. When glycerol alone or glycerol and trehalose were added to the admixture and then homogenized, results from stirring experiments again showed that these formulations were unstable with extensive crystallization observed over time. Thus, adding bulking agents or PVP to either the admixture or to the heated homogenate does not result in stabilization of the metastable formulation under stirring conditions.

Spray drying of molten microparticles of fenofibrate in the presence of a phospholipid stabilizing agent and a bulking agent produces a novel composition that when formulated into a suitable dosage form as a dried solid optionally in the presence of one or more excipients such as sucrose, sorbitol, trehalose, Tween 80, mannitol, other sugars and starch, and the like provides a novel oral dosage form of the drug which when taken by a fasting or a fed patient exhibits a differential uptake of the drug by the fasted patient of at least 80% of the AUC amount of drug taken up by a patient fed a high fat meal. The reduction in food effect on the uptake of drug by fasted and fed patients is useful in the prescription of the drug to a patient undergoing treatment in that the patient will receive comparable and therapeutically useful levels of the drug regardless of whether the patient is fed or fasted.

The mechanism of obviation of food effect in a patient taking the dosage form of fibrate in this invention is not yet fully understood, but it can be postulated that the phospholipid is uniquely involved in several aspects that lead to this novel discovery. For example, the phospholipid is involved in the stabilization of the fibrate particles during their formation and manipulation during formation of the dosage form; the phospholipid is involved in the reconstitution and continued stabilization of the particles during disintegration of the oral dosage form in vivo; and the phospholipid is perhaps involved in a mechanism leading to dissolution of the particles in vivo and/or uptake of the drug into the blood, e.g., molecular association between phospholipid and drug and other in vivo substance in some sort of transport mechanism.

Microscopically, heated homogenate particles of fenofibrate are non-crystalline.

In another aspect of this invention, more than one surface active substance can be used to prepare formulations according to this invention. At least one surface active substance is needed to prepare the initial admixture of this invention, and in one aspect can suffice in the preparation of subsequent heated suspensions and heated homogenates, and spray dried particles prepared according to this invention.

Addition of more than one surface active substance can be made to the admixture, the heated suspension, or the heated homogenate of this invention. Such additions can be made at one individual step in the process or at more than one step in the process. For example, a second surface active agent can be added to the admixture or to the heated suspension.

The total concentration of one or of more than one surface active substance added to the formulations prepared according to this invention can be in the range of 0.1 to 50%, preferably 0.2 to 20%, and more preferably 0.5 to 10%.

In another aspect of this invention, bulking agents can be added to the admixture and/or to the heated homogenate. Bulking agents can be added as solids, as mixtures, as solutions in aqueous carrier, and in combinations of solids and solutions. Bulking agents can be added at the beginning or end of the steps leading to the formation of a heated homogenate. They can be added at more than one stage during the process. The amount of total bulking agents that can be added ranges from about 0.1% to about 50%, preferably from 1% to about 25%, and more preferably from about 2% to about 20%. Bulking agents can be added as individual agents at these levels or in combination such that the total amount of bulking agent resides within these levels.

In one aspect, a preferred bulking agent can be selected from the group consisting of mannitol, sucrose, trehalose, sorbitol, and mixtures thereof. Additional pharmaceutically acceptable excipients such as Ac-Di-Sol and Cab-O-Sil can be added prior to spray drying.

Spray drying of the heated homogenate can be accomplished using a commercially available spray drying apparatus such as a LabPlant SD05 Spray Dryer or using a larger scale spray drying apparatus. Preferably, dry air or dry oxygen free air or nitrogen or other non-oxidizing non-reactive dry gas is used in the spray drying. Moisture level in the isolated spray dried powder obtained as an initial product in the spray drying process is preferably below 3%, more preferably below 2%, and most preferably below 1%. Moisture level can be measured by a Karl Fisher method.

Bulking agents can be added to the formulation to facilitate reconstitution. In a preferred embodiment, bulking agents can be selected from the group consisting of mannitol, sucrose, sorbitol, trehalose, and combinations thereof. The amount of bulking agent present in the formulation can range from about 1% to about 50% or more. In a preferred embodiment, the amount of bulking agent can range from about 2% to about 20%, and in a more preferred embodiment, the amount of bulking agent can range from about 3% to about 15%.

In one aspect, the dried material can comprise phospholipid-stabilized particles in a bulking agent that is substantially amorphous. For example, the dried material can comprise phospholipid-stabilized particles of fenofibrate in substantially amorphous sucrose, in substantially amorphous mannitol, in substantially amorphous lactose, in a substantially amorphous mixture of sucrose and raffinose, in a substantially amorphous mixture of sucrose and sorbitol, in a substantially amorphous mixture of sucrose and raffinose and sorbitol. In a preferred embodiment, the dried material comprises phospholipid-stabilized particles of fenofibrate in a substantially amorphous bulking agent such as those listed previously, wherein the dried material contains from about 0.1% to about 3% of adsorbed water, more preferably 0.1% to about 2% of adsorbed water, and most preferably 0.1% to about 1% of adsorbed water. These values are below the absorption isotherm of an amorphous sugar containing microparticles of phospholipid stabilized fenofibrate. In one aspect, a spray dried formulation containing phospholipid-stabilized particles of fenofibrate in a substantially amorphous bulking agent will maintain its amorphous character if the amount of water present in the initially spray dried formulation is not increased for example by exposure to humidity that would lead to increased moisture content in the dried material and facilitate crystal growth. The rate of conversion of amorphous bulking agent to crystalline bulking agent can be enhanced by increasing the temperature and humidity to which the dried amorphous material is exposed. The rate of conversion of amorphous bulking agent to crystalline bulking agent can be reduced by decreasing the temperature and humidity to which the dried amorphous material is exposed.

In one theory, the rate of conversion of amorphous bulking agent to crystalline bulking agent can be related to the water absorption isotherm of the dried system that comprises the amorphous bulking agent, the phospholipid, and other excipients present in the formulation. If the amount of water or level of humidity to which the dried formulation is exposed is below the adsorption isotherm at a given temperature, the bulking agent will remain substantially amorphous and conversion to crystalline material will be relatively slow, preferably remaining substantially unchanged over 6 months, more preferably over 12 months, even more preferably over 18 months, and most preferably over 24 months; if the amount of water (humidity) to which the dried formulation is exposed is above the absorption isotherm at a given temperature, the amorphous material will tend to convert relatively rapidly to a crystalline material. The higher the level of humidity, the faster the conversion. The higher the temperature, the faster the conversion. A preferred keeping condition for an amorphous material of this invention is thus about 4° C. to about 40° C. at a relative humidity level that is below the absorption isotherm of the amorphous material, more preferably from about 4° C. to about 30° C. at a relative humidity level that is below the absorption isotherm of the amorphous material, even more preferably from about 4° C. to about 25° C. at a relative humidity level that is below the absorption isotherm of the amorphous material, and most preferably from about 4° C. to about 20° C. at a relative humidity level that is below the absorption isotherm of the amorphous material.

The dried amorphous material can be prepared by spray drying. In this embodiment, the amorphous material can comprise a bulking agent in which the particles are suspended wherein the bulking agent is present as a bead. The bead can contain regions of crystalline bulking agent in addition to the particles of phospholipid stabilized microparticles. The amount of crystalline material can range from substantially zero to about 95% of the bulking agent, but is preferably less than 50%, more preferably less than 20%.

In another aspect, the spray dried material can comprise phospholipid-stabilized particles in a bulking agent that is substantially crystalline. For example, the dried material can comprise phospholipid-stabilized particles of fenofibrate in substantially crystalline mannitol or substantially crystalline calcium phosphate.

By small particles containing fenofibrate is meant particles in the range of 0.1 micron to 10 micrometers in average diameter containing fenofibrate, preferably in the range of 0.1 to 5 micrometers containing fenofibrate, and most preferably in the range of 0.1 to 2 micron containing fenofibrate.

In one aspect, addition of bulking agents such as sucrose, mannitol, trehalose, sorbitol and the like prior to spray drying provides particle size suspensions on reconstitution similar in size to those of the antecedent cooled dispersion. The presence of added water-insoluble excipients of sizes larger than the phospholipid stabilized fenofibrate microparticles present can be detected in particle size distribution measurements, but a size distribution of the microparticles of fenofibrate in the excipient-containing dried material will be substantially similar to that of the suspension of microparticles before drying.

Formulations prepared by this invention can be spray dried into powders which can be resuspended or filled into capsules or converted into granules or tablets with the addition of binders and other excipients known in the art of tablet making such as, for example, silica as a flow aid and magnesium stearate. A preferred capsule formulation for oral administration of phospholipid stabilized fenofibrate microparticles comprises fenofibrate (10% w/w) as microparticles prepared by microfluidization in 10 mM phosphate buffer with phospholipid Lipoid E80 (3% w/w), sucrose (10% w/w), and sorbitol (5% w/w). Other preferred formulations comprise fenofibrate (10%) as microparticles stabilized by phospholipid (e.g., Lipoid E80 at 0.5 to about 3%), and mannitol or sucrose (5% to 15%).

A suspension of microparticles such as one prepared by microfluidization of these ingredients is dried by spray drying, optionally after being mixed with additional excipients such as Ac-Di-Sol, Cab-O-Sil, or other pharmaceutically acceptable excipients, to remove water and to form a solid which is blended with additional excipients and tableting agents known in the art such as colloidal silicon dioxide (about 1% w/w) and magnesium stearate (about 5% w/w). This blend is then filled into capsules or compressed into tablets for oral delivery. The amount of fenofibrate per unit oral dosage form such as per capsule or tablet can range from about 50 mg to about 300 mg, but is preferably 50 mg, 67 mg, 100 mg, 134 mg, 150 mg, 160 mg, 200 mg, 213 mg, 250 mg, and 300 mg. Useful dosage levels for tablets and capsules include in the high end of the range milligram levels that are divisible by three such as 150 mg (giving related lower dosage levels of 100 mg and 50 mg), 159 mg (giving related lower dosage levels of 106 mg and 53 mg), 156 mg (giving related lower dosage levels of 104 mg and 52 mg), 153 mg (giving related lower dosage levels of 102 mg and 51 mg). Multiples of this type have the advantage of assisting a physician to titrate a patient to a therapeutically acceptable level starting with a low dose of the fibrate and changing the dose in well defined increments until a desired result is achieved, such as a lowering of levels of cholesterol and low density lipoproteins. Additional preferred dosage levels contain 50 mg, 67 mg, 100 mg, 134 mg, 150 mg, 160 mg, 200 mg and 213 mg of fenofibrate as microparticles stabilized with phospholipid.

Tablets and capsules and powders containing microparticles of fenofibrate of this invention can be packaged in bottles or blister packs or in other packaging for use by a human in need of treatment by fenofibrate. Preferably the packaging is sealed to substantially prevent the exposure of the tablets or capsules or powders to moisture. A blister packaging comprising aluminum foil sealed to exclude air containing moisture is a preferred packaging. A reclosable bottle or jar or other container comprising a lid or top or stopper as a closing means is preferably suitable if the closing means forms a seal with the remainder of the container that substantially prohibits the admission of air containing moisture to the contents which comprise the dried powders or tablets or capsule dosage forms of this invention. In a preferred container, a dessicant such as silica contained in a moisture permeable package such as a closed sac or bag is present in the container proximal to the dosage forms to preferentially adsorb moisture.

Capsules and tablets and powders and granules of this invention for oral administration provide fenofibrate to a human patient in need of treatment by fenofibrate that is relatively independent of a food effect. Thus, a patient in a fasted state will receive at least 80% of the dose of the drug active species that a patient in a fed state will receive by taking the same capsule or tablet or powder or granular dosage form (at the same level of drug per unit dosage form, i.e., at the same number of mg of drug per tablet or capsule given to the same patient when fasted as when fed). More preferably, a patient in a fasted state will receive at least 85% of the dose of the drug active species that a patient in a fed state will receive by taking the same capsule or tablet or powder or granular dosage form. Even more preferably, a patient in a fasted state will receive at least 87% of the dose of the drug active species that a patient in a fed state will receive by taking the same capsule or tablet or powder or granular dosage form. Even more preferably, a patient in a fasted state will receive at least 90% of the dose of the drug active species that a patient in a fed state will receive by taking the same capsule or tablet or powder or granular dosage form. Even more preferably, a patient in a fasted state will receive at least 95% of the dose of the drug active species that a patient in a fed state will receive by taking the same capsule or tablet or powder or granular dosage form.

Capsules and tablets prepared from spray dried microparticles of molten fenofibrate for oral administration and optionally containing a statin provide fenofibrate to a human patient in need of treatment that is substantially independent of food effect. Thus, a patient in a fasted state will receive at least 80% of the dose of the drug that the patient in a fed state will receive by taking the same capsule or tablet dosage form. More preferably, a patient in a fasted state will receive at least 85% of the dose of the drug that the patient in a fed state will receive by taking the same capsule or tablet dosage form. Even more preferably, a patient in a fasted state will receive at least 87% of the dose of the drug that the patient in a fed state will receive by taking the same capsule or tablet dosage form. Even more preferably, a patient in a fasted state will receive at least 90% of the dose of the drug that the patient in a fed state will receive by taking the same capsule or tablet dosage form. Yet even more preferably, a patient in a fasted state will receive at least 95% of the dose of the drug that the patient in a fed state will receive by taking the same capsule or tablet dosage form.

The amount of a given statin in a dosage form of this invention can be the same as the amount of that statin in currently available dosage forms of that statin alone such as those listed previously, or it can be an amount that is lower than the amount of that statin in currently available dosage forms of that statin alone. The presence of the statin augments or supplements the effect of the spray dried fenofibrate of this invention, and the presence of the spray dried fenofibrate augments or supplements the effect of the statin. Thus, a therapeutically effective dosage form of this invention containing a statin and spray dried microparticles of fenofibrate can have relatively lower amounts of the statin, relatively lower amounts of fenofibrate, or relatively lower amounts of both than the amount of the statin when in a dosage form without fenofibrate or than the amount of fenofibrate when in a dosage form without the statin, or both.

The dosage forms of this invention can be prepared by a process comprising blending spray dried small particles containing fenofibrate stabilized by a phospholipid surface active substance in a bulking agent with a statin and optionally with one or more pharmaceutically acceptable excipients such a one or more sugars (e.g., sucrose, raffinose, sorbitol, and trehalose).

The dosage forms of this invention can be prepared by a process comprising blending spray dried small particles containing fenofibrate stabilized by a phospholipid surface active substance in a bulking agent with a statin and with a bulking agent comprising a sugar and optionally with one or more pharmaceutically acceptable excipients such a one or more additional sugars (e.g., sucrose, raffinose, sorbitol, and trehalose).

Dosage forms of this invention can be administered to a patient in need of treatment by a combination of a statin and spray dried small particles containing fenofibrate of this invention can be administered several times a day such as three or four times a day, but more preferably twice a day, and most preferably once a day. Preferably, the more frequent the administration of the drug, the smaller the quantity of the drug contained in a given dosage form.

The tablets containing the fibrate dosage form of this invention can be prepared by compression of solid particles in a bulking agent such as a sugar as described herein. Optionally, the tablets can be coated with a pharmaceutically acceptable coating material such as pharmaceutically acceptable polymer for example carboxymethyl cellulose, sodium carboxymethyl cellulose, povidone, PVP, polyethylene, PEG, shellac, cellulose acetate, CAP, polyvinyl acetate phthalate, PVAP, hydroxypropyl methyl cellulose phthalate, HPMCP, polymers of methacrylic acid and its esters, Eudragit polymers, methyl cellulose, MC, ethyl cellulose, EC, hydroxyethyl cellulose, HEC, methylhydroxyethyl cellulose, MHEC, hydroxypropyl cellulose, HPC, hydroxypropylmethyl cellulose, BPMC, and combinations thereof and at levels well known in the art of tablet coating. The coatings can be applied in pharmaceutically acceptable form which is well known in the art such as suspension coating, fluid bed coating, spray coating, Escaravage coating which is coating method for individual tablets using a solution of coating materials applied with a brush, film coating, preferably from a water based solution and optionally from a water-solvent such as water-ethanol based solution, and dried to form a dried, film-coating. The added weight to the tablet can be from about 0.1% to about 20%, preferably from 1% to about 5%. The solutions used to coat the tablet dosage form can of course optionally contain mixtures of ingredients such as sugars, pharmaceutically acceptable plastisizers, antioxidants, pH modifiers such as carboxylic acids or carboxylate salts, vitamin E, beta-carotene, and the like. The coating can be applied in a single layer or optionally in several layers with each layer being the same composition or a different composition of ingredients.

The formulations of this invention comprising spray dried phospholipid stabilized microparticles of fenofibrate in the presence of a bulking agent formulated in a dosage form of fenofibrate (tablet, capsule, powder, dispersion of particles in a fluid, dispersion of particles in a nutrient such as a low fat food bar or other means of administering the particles) can be taken with or without food, especially when such food contains fat, to provide blood levels of fenofibrate active agent (i.e., fenofibric acid) that are substantially independent of the amount of food or fat in food (including fasting or zero fat, low fat, and high fat meals) taken proximal to the administration of the fenofibrate dosage form. This is a surprising result in view of the known food effect associated with other dosage forms of fenofibrate such as micronized fenofibrate and fenofibrate micronized in the presence of a solid surfactant such as sodium lauryl sulfate.

While a preferred method of preparation of spray dried microparticles of fenofibrate stabilized with phospholipid comprises a microfluidization process using molten microdroplets or molten microparticles of fenofibrate, other methods of preparation of microparticles of fenofibrate can find utility in this invention. For example, it is possible to prepare molten microparticles of fenofibrate stabilized with phospholipid using a sonication process; using a milling process such as heated media milling, heated ball milling, and the like; using a heated precipitation process such as precipitation of drug from a solvent miscible with water heated above the melting point of the drug in the presence of a phospholipid to form a suspension of molten microparticles; and using a heated emulsification process at a temperature above the melting point of the drug. Microparticles of fenofibrate prepared according to these known methods and stabilized with a phospholipid can be formulated with a statin in the presence of the bulking agents and prepared into dosage forms for use in patients as described herein.

The invention is additionally illustrated in connection with the following examples, which are considered to be illustrative of the present invention. It should be understood, however, that the invention is not limited to the specific details of the Examples.

EXAMPLE 1

An admixture of 3% Lipoid E80 as the surface active substance and 10% fenofibrate is homogeneously dispersed 10 mM pH 8.0+/−0.2 aqueous phosphate buffer using a ProScientific 400 high shear mixer at 2,000 to 3,600 rpm at ambient temperature for 30 minutes. Sucrose (10%) is then added and the admixture is heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained at 85° C. to 99° C. to form a heated homogenate containing the drug. After 10 passes, the heated homogenate is then spray dried to produce a dried powder containing Lipoid E80 stabilized microparticles of fenofibrate in sucrose.

EXAMPLE 2

An admixture of 3% Lipoid E80 as the surface active substance and 10% fenofibrate is homogeneously dispersed 10 mM pH 8.0+/−0.2 aqueous phosphate buffer using a ProScientific 400 high shear mixer at 2,000 to 3,600 rpm at ambient temperature for 30 minutes. Mannitol (10%) is then added and the admixture is heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained at 85° C. to 99° C. to form a heated homogenate containing the drug. After 10 passes, the heated homogenate is then spray dried to produce a dried powder containing Lipoid E80 stabilized microparticles of fenofibrate in mannitol.

EXAMPLE 3

The procedure of example 1 is repeated using 7% sucrose plus 0.5% raffinose.

EXAMPLE 4

The dried small particles containing fenofibrate prepared in each of Examples 1 to 3 are blended with 2% Cabosil, 5% sucrose, and 0.25% magnesium stearate. After thorough blending, the mixture is compressed, optionally with an intermediate formation of compressed slugs of the composition which are milled, optionally sieved to a uniform particle size range, and then recompressed into tablets for oral dosing. The tablets are prepared at the following dosage levels of fenofibrate and are sized according to volumes encountered.

50 mg
51 mg
52 mg
53 mg
54 mg
67 mg
100 mg
102 mg
104 mg
106 mg
134 mg
150 mg
153 mg
156 mg
159 mg
160 mg
200 mg
213 mg
250 mg
300 mg

EXAMPLE 5

Gelatin capsules are filled with the dried small particles containing fenofibrate prepared in each of Examples 1 to 3 and sealed to provide capsules for oral dosing. The capsules are filled at the following dosage levels of fenofibrate and are sized according to volumes encountered.

50 mg
51 mg
52 mg
53 mg
54 mg 67 mg
100 mg
102 mg
104 mg
106 mg
134 mg
150 mg
153 mg
156 mg
159 mg
160 mg
200 mg
213 mg
250 mg
300 mg

EXAMPLE 6

The following formulations are prepared according to the method of example 1 leading to a heated homogenate before drying consisting of:

21-1) 9% fenofibrate, 3% Lipoid E80, 10% sucrose;
21-2) 10% fenofibrate, 3% Lipoid E80, 12% sucrose, 5% sorbitol;
21-3) 10% fenofibrate, 3.5% Lipoid E80, 12% sucrose, 1% sorbitol;
21-4) 9% fenofibrate, 2.7% Lipoid E80, 19% sucrose, 4.5% sorbitol.

The formulations are spray dried in a commercially available spray dryer consisting of a chamber with inside diameter of 1.22 meters and a cylindrical height of 1.14 meters with a 60° conical bottom. Electrically heated air is used as the process gas admitted via a ceiling disperser. Each spray dried formulation is isolated initially as a dried powder that can be handled in a dry atmosphere without caking.

EXAMPLE 7

A mixture of Lipoid E80 and fenofibrate is homogeneously dispersed in 10 mM pH 8.0+/−0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then batchwise homogenized in 3 to 10 batch volume cycles using a Microfluidizer M110Y operated at 3,400 to 3,600 psig while maintained at 85° C. to 99° C. to form a heated homogenate containing the drug. The heated homogenate is then treated with bulking agents and excipients listed in the table below, mixed at the molten fenofibrate temperature, and then dried by spray drying in the molten state. The following compositions (in wt %) are prepared by this method.

Spray dried powders (100 parts) are blended with excipients Avicel-PH102 (18.5 parts), Ac-Di-Sol (3.95 parts), Cab-O-Sil (0.62 parts), and magnesium stearate (0.25 parts), processed into 1 mm granules or slugs by preliminary compression of the blend followed by crushing and sieving (USP Standard #14 sieve), blended with additional magnesium stearate, and then compressed into tablet dosage forms. Hardness of the tablets produced in different batches ranges from 2 to 9 KPa either in an automatic tableting machine or by manual compression using a CMS-15 tablet press (Cadmach Machinaries).

What is claimed is:

1. A process for the preparation of small particles or microparticles containing fenofibrate and a phospholipid surface stabilizing substance comprising the steps of:
   a) mixing at high shear an admixture of fenofibrate and a phospholipid in an aqueous carrier in the absence of an organic solvent and optionally in the presence of one or more than one surface active substances within a temperature range at or above the melting point of the fenofibrate to form a heated suspension containing the fenofibrate, then
   b) homogenizing said heated suspension in a pressure range and within said temperature range to form a heated homogenate containing the fenofibrate then
   c) spray drying the heated homogenate to form dried small particles containing the fenofibrate wherein one or more bulking agents is added at any stage of either of steps (a) or (b) and wherein at least one surface active agent is a phospholipid.

2. The process of claim 1 wherein the bulking agent is selected from the group consisting of a monosaccharide, a disaccharide, a trisaccharide, lactose, mannitol, sorbitol, trehalose, glycerol, dextrose, fructose, xylitol, and mixtures thereof.

3. The process of claim 1 wherein the bulking agent is selected from the group consisting of sucrose, lactose, mannitol, sorbitol, trehalose, and mixtures thereof.

4. The process of claim 1 wherein the surface active agent is a phospholipid selected from the group consisting of Lipoid E80, Lipoid EPC, Lipoid SPC, DMPG, Phospholipon 100H, Lipoid SPC-3, and mixtures thereof.

5. The process of claim 1 wherein the surface active agent is Lipoid E80.

6. The process of claim 1 wherein the temperature range is from the melting point of fenofibrate to 20° C. higher than the melting point of fenofibrate.

7. The process of claim 1 wherein the aqueous carrier is selected from the group consisting of water and buffered water wherein the pH of the buffer is from 4 to 10.

8. The process of claim 1 wherein the aqueous carrier is phosphate buffered water having a pH from 7 to 9.

9. The process of claim 1 wherein the aqueous carrier is phosphate buffered water having a pH from 7.5 to 8 5.

10. The process of claim 1 wherein the pressure range is from 2,000 to 30,000 psi.

| Suspension No. | Fenofibrate | Lipoid E80 | Sucrose | Mannitol | Ac-Di-Sol | Cab-O-Sil (colloidal silica) |
|---|---|---|---|---|---|---|
| 7-a | 10.0 | 0.5 | 17.5 | | | |
| 7-b | 10.0 | 0.5 | 17.5 | | 1.8 | |
| 7-c | 10.0 | 0.5 | 17.5 | | | 0.5 |
| 7-d | 10.0 | 0.5 | 7 | | 3 | 0.5 |
| 7-e | 10.0 | 0.5 | | 7 | 3 | 0.5 |
| 7-f | 10.0 | 0.5 | 17.5 | | 1.8 | 0.5 |

11. The process of claim 1 wherein the small particles containing fenofibrate have an average size in the range from 0.1 to 10 micrometers.

12. The process of claim 1 wherein the small particles containing fenofibrate have an average size in the range from 0.1 to 5 micrometers.

13. The process of claim 1 wherein the small particles containing fenofibrate have an average size in the range from 0.1 to 2 micrometers.

14. A composition comprising microparticles containing fenofibrate and a phospholipid surface stabilizing substance that is prepared according to the process of claim 1 further containing from 0.1 to about 5% water.

15. An orally administered pharmaceutical composition comprising microparticles containing fenofibrate and a phospholipid surface stabilizing substance prepared according to the process of claim 1, wherein a therapeutically effective amount of said pharmaceutical composition provides a quantity of fenofibrate active species to a fasted human patient in need of treatment by said fenofibrate that is greater than 90% of the quantity of said fenofibrate active species provided by said amount to said patient when fed a high fat meal.

16. A capsule or tablet or powder or granular dosage form for oral administration comprising microparticles containing fenofibrate and a phospholipid surface stabilizing substance prepared according to the process of claim 1 wherein said amount of said dosage form provides a level of fibrate active species into the blood of a patient in a fasted state that differs by less than 25% of the level of said fibrate active species that said patient receives in a fed state.

17. A capsule or tablet or powder or granular dosage form for oral administration comprising microparticles containing fenofibrate and a phospholipid surface stabilizing substance prepared according to the process of claim 1 wherein said amount of said dosage form provides a level of fibrate active species into the blood of a patient in a fasted state that differs by less than 20% of the level of said fibrate active species that said patient receives in a fed state.

18. A capsule or tablet or powder or granular dosage form for oral administration comprising microparticles containing fenofibrate and a phospholipid surface stabilizing substance prepared according to the process of claim 1 wherein said amount of said dosage form provides a level of fibrate active species into the blood of a patient in a fasted state that differs by less than 15% of the level of said fibrate active species that said patient receives in a fed state.

19. A capsule or tablet or powder or granular dosage form for oral administration comprising microparticles containing fenofibrate and a phospholipid surface stabilizing substance prepared according to the process of claim 1 wherein said amount of said dosage form provides a level of fibrate active species into the blood of a patient in a fasted state that differs by less than 10% of the level of said fibrate active species that said patient receives in a fed state.

20. A capsule or tablet or powder or granular dosage form for oral administration comprising microparticles containing fenofibrate and a phospholipid surface stabilizing substance prepared according to the process of claim 1 wherein said amount of said dosage form provides a level of fibrate active species into the blood of a patient in a fasted state that differs by less than 5% of the level of said fibrate active species that said patient receives in a fed state.

21. A tablet dosage form of claim 16 that further comprises a dried film-coating formed by application of a water based solution the dosage form.

22. A tablet dosage form of claim 16 that further comprises a pharmaceutically acceptable polymer in a coating.

23. A tablet dosage form claim 16 that further comprises a pharmaceutically acceptable carbohydrate in a coating.

24. The tablet dosage form of claim 23 where the carbohydrate in the coating is a sugar.

25. The dosage form of claim 16 further comprising one or more excipients selected from the group consisting of monosaccharides, disaccharides, disaccharides, raffinose, lactose, mannitol, sorbitol, trehalose, glycerol, dextrose, maltodextrose, fructose, xylitol, and mixtures thereof.

26. The dosage form of claim 16 wherein the phospholipid surface stabilizing substance comprises a mixture of phospholipids.

27. The dosage form of claim 16 wherein the phospholipid surface stabilizing substance is selected from the group consisting of egg phospholipid, Lipoid E80, Lipoid EPC, Lipoid SPC, DMPG, Phospholipon 100H, a hydrogenated soybean phosphatidylcholine, Phospholipon 90H, Lipoid SPC-3, and mixtures thereof.

28. The dosage form of claim 16 wherein the fenofibrate is crystalline.

29. The dosage form of claim 16 wherein the microparticles are smaller than 5 micrometers.

30. The dosage form of claim 16 wherein the microparticles are smaller than 4 micrometers.

31. The dosage form of claim 16 wherein the microparticles are smaller than 3 micrometers.

32. The dosage form of claim 16 wherein the microparticles are smaller than 2 micrometers.

33. The dosage form of claim 16 wherein the microparticles are smaller than 1 micrometers.

34. The dosage form of claim 16 to further containing from 0.1 to about 5% water.

35. The dosage form of claim 16 wherein the therapeutically effective amount is selected from the group consisting of 50 mg of fenofibrate, 51 mg of fenofibrate, 52 mg of fenofibrate, 53 mg of fenofibrate, 54 mg of fenofibrate, 67 mg of fenofibrate, 100 mg of fenofibrate, 102 mg of fenofibrate, 103 mg of fenofibrate, 104 mg of fenofibrate, 134 mg of fenofibrate, 150 mg of fenofibrate, 153 mg of fenofibrate, 156 mg of fenofibrate, 159 mg of fenofibrate, 160 mg of fenofibrate, 200 mg of fenofibrate, 213 mg of fenofibrate, 250 mg of fenofibrate, and 300 mg of fenofibrate.

36. An orally administered pharmaceutical composition comprising microparticles containing fenofibrate and a phospholipid surface stabilizing substance prepared according to the process of claim 1 wherein a therapeutically effective amount of said orally administered pharmaceutical composition provides a quantity of fenofibrate active species to a fasted human patient in need of treatment by fenofibrate that is greater than 85% of the quantity of fenofibrate active species provided by said amount to said patient when fed at least 1000 calories 50% of which are from fat.

37. An orally administered pharmaceutical composition comprising microparticles containing fenofibrate and a phospholipid surface stabilizing substance prepared according to the process of claim 1 wherein a therapeutically effective amount of said orally administered pharmaceutical composition provides a quantity of fenofibrate active species to a fasted human patient in need of treatment by fenofibrate that is greater than 90% of the quantity of fenofibrate active species provided by said amount to said patient when fed at least 1000 calories 50% of which are from fat.

38. An orally administered pharmaceutical composition comprising microparticles containing fenofibrate and a phospholipid surface stabilizing substance prepared according to the process of claim 1 wherein a therapeutically effective amount of said orally administered pharmaceutical composition provides a quantity of fenofibrate active species to a fasted human patient in need of treatment by fenofibrate that is greater than 95% of the quantity of fenofibrate active species provided by said amount to said patient when fed at least 1000 calories 50% of which are from fat.

39. The orally administered pharmaceutical composition of claim 36 further comprising one or more excipients selected from the group consisting of monosaccharides, disaccharides, trisaccharides, raffinose, lactose, mannitol, sorbitol, trehalose, glycerol, dextrose, maltodextrose, fructose, xylitol, and mixtures thereof.

40. The orally administered pharmaceutical composition of claim 36 wherein the phospholipid surface active substance is selected from the group consisting of egg phospholipid, Lipoid E80, Lipoid EPC, Lipoid SPC, DMPG, Phospholipon 100H a hydrogenated soybean phosphatidylcholine, Phospholipon 90H, Lipoid SPC-3, and mixtures thereof.

41. The process of claim 1 wherein the surface active agent phospholipid is present in an amount from about 0.1% to about 15%.

42. The process of claim 1 wherein the surface active agent phospholipid is present in an amount from about 05% to about 5%.

43. The process of claim 1 wherein the dried small particles further contain from 0.1 to 5% water.

44. The process of claim 1 wherein the dried small particles further contain from 0.1% to 3% water.

45. The process of claim 1 wherein the dried small particles further contain from 0.1% to 2% water.

46. The process of claim 1 wherein the dried small particles further contain from 0.1% to 1% water.

47. A method of treating dyslipidemia and dyslipoproteinemia in a mammal which comprises administering to said mammal once a day a therapeutically effective oral dosage form comprising microparticles containing fenofibrate and a phospholipid surface stabilizing substance prepared according to the process of claim 1 wherein said dosage form provides into the blood of said patient in a fasted state a therapeutically effective amount of fenofibrate active species that is at least 90% of the AUC amount of fenofibrate active species provided by said dosage form into the blood of said patient in a fed state.

48. The method of claim 47 wherein dyslipidemia comprises hypercholesterolemia, hyperlipidemia, hypertrigylceridaemia or combinations thereof.

49. The process of claim 1 where the heated homogenate further comprises a statin added thereto.

50. The process of claim 49 wherein the statin is selected from the group consisting of lovastatin, pravastatin, simvastatin, atorvastatin, rosuvastatin, fluvastatin, itavastatin, and cerivastatin.

51. A composition comprising microparticles containing fenofibrate and a phospholipid surface stabilizing substance that is prepared according to the process of claim 1 further containing a statin.

52. The composition of claim 51 wherein the statin is selected from the group consisting of lovastatin, pravastatin, simvastatin, atorvastatin, rosuvastatin, fluvastatin, itavastatin, and cerivastatin.

53. The orally administered pharmaceutical composition of claim 15 further comprising a statin present in a therapeutically effective dose range.

54. orally administered pharmaceutical composition of claim 53 wherein the statin is to be selected from the group consisting of lovastatin, pravastatin, simvastatin, atorvastatin, rosuvastatin, fluvastatin, itavastatin., and cerivastatin.

55. The capsule or tablet or powder or granular dosage form of claim 16 further comprising a statin present in a therapeutically effective dose range.

56. The capsule or tablet or powder or granular dosage form of claim 5 wherein the statin is selected from the group consisting of lovastatin, pravastatin, simvastatin, atorvastatin, rosuvastatin, fluvastatin, itavastatin, and cerivastatin.

57. The orally administered pharmaceutical composition of claim 36 further comprising a statin present in a therapeutically effective dose range.

58. The orally administered pharmaceutical composition of claim 57 wherein the statin is selected from the group consisting of lovastatin, pravastatin, simvastatin, atorvastatin, rosuvastatin, fluvastatin, itavastatin, and cerivastatin present in a therapeutically effective dose range.

59. The method of claim 47 further comprising a statin present in a therapeutically effective dose range.

60. The method of claim 59 wherein the statin is selected from the group consisting of lovastatin, pravastatin, simvastatin, atorvastatin, rosuvastatin, fluvastatin, itavastatin, and cerivastatin.

* * * * *